(12) United States Patent
Im et al.

(10) Patent No.: US 7,777,003 B2
(45) Date of Patent: Aug. 17, 2010

(54) RECOMBINANT CHIMERIC ACETYLCHOLINE RECEPTORS AND THEIR DERIVATIVES RECOGNIZED BY CD4 T CELLS OF MYASTHENIC PATIENTS FOR THE TREATMENT OF MYASTHENIA GRAVIS

(75) Inventors: Sin Hyeog Im, Gwangju (KR); Hwa Joong Yi, Gwangju (KR); Jae Seon So, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 11/421,433

(22) Filed: May 31, 2006

(65) Prior Publication Data

US 2007/0072264 A1 Mar. 29, 2007

(51) Int. Cl.
C07K 14/705 (2006.01)
C07K 19/00 (2006.01)
(52) U.S. Cl. .......................................... 530/350; 514/2
(58) Field of Classification Search ....................... None
See application file for complete search history.

(56) References Cited

U.S. PATENT DOCUMENTS 6,936,457 B1 * 8/2005 Gillespie et al. ......... 435/252.3
2002/0081652 A1 6/2002 Fuchs et al.

OTHER PUBLICATIONS

Beeson et al., The human muscle nicotinic acetylcholine receptor alpha-subunit exists as two isoforms: a novel exon. EMBO J., 9, 2101-2106, 1990.*
Im et al., Protective molecular mimicry in experimental myasthenia gravis. J. Neuroimmunol., 126, 99-106, 2002.*
Lennon et al., Recombinant Human Acetylcholine Receptor alpha-Subunit Induces Chronic Experimental Autoimmune Myasthenia Gravis, J Immunol., 146, 2245-2248, 1991.*
Yoshikawa et al., A 17-Mer Self-peptide of Acetylcholine Receptor Binds to B Cell MHC Class II, Activates Helper T Cells, and Stimulates Autoantibody Production and Electrophysiologic Signs of Myasthenia Gravis, J. Immunol., 159, 1570-1577, 1997.*
Moioa et al. Residues of the alpha and gamma Subunits of Muscle Acetylcholine Receptor Involved in Formation of Immunodominant CD4+ Epitopes, May 1, 1994, Journal of Immunology 152(9):4686-4698.*

Tzartos et al. Localization of the Main Immunogenic Region of Human Muscle Acetylcholine Receptor to Residues 67-76 of the alpha Subunit. May 1, 1988, P.N.A.S. 85(9):2899-2903.*
Zisman et al. Peptide Analogs to Pathogenic Epitopes of the Human Acetylcholine Receptor alpha Subunit as Potential Modulators of Myasthenia Gravis, Apr. 30, 1996, P.N.A.S. 93(9):4492-4497.*
Im et al., "Role of Tolerogen Conformation in Induction of Oral Tolerance in Experimental Autoimmune Myasthenia Gravis," Journal of Immunology, 165: 3599-3605 (2000).
Im et al., "Suppression of Ongoing Experimental Myasthenia by Oral Treatment With an Acetylcholine Receptor Recombinant Fragment," Journal of Clinical Investigation, 104(12): 1723-1730 (1999).
Im et al., "Mechanism of Nasal Tolerance Induced by a Recombinant Fragment of Acetylcholine Receptor for Treament of Experimental Myasthenia Gravis," Journal of Neuroimmunology, 111: 161-168 (2000).
Maiti et al., "Immunosuppression of Rat Myasthenia Gravis by Oral Administration of a Syngeneic Acetylcholine Receptor Fragment," Journal of Neuroimmunology, 152: 112-120 (2004).
Bartfeld and Fuchs, "Specific Immunosuppression of Experimental Autoimmune Myasthenia Gravis by Denatured Acetylcholine Receptor," Neurobiology, 75(8): 4006-4010 (1978).
Zhong et al., "Multiantigen/Multiepitope-Directed Immune-Specific Suppression of "Complex Autoimmune Encephalomyelitis" By a Novel Protein Product of a Synthetic Gene," Journal of Clinical Investigation, 110: 81-90 (2002).
Im et al., "Immunomodulation of Ongoing Experimental Myasthenia by Tolerance Induction With B-Cell Epitopes Free Recombinant Acetylcholine Receptor," Jun. 24, 2005, Abstract from Korean Brain Society (with English Abstract).

* cited by examiner

Primary Examiner—John D Ulm
(74) Attorney, Agent, or Firm—JHK Law; Joseph Hyosuk Kim

(57) ABSTRACT

The present invention relates to recombinant acetylcholine receptor polypeptides recognized by CD4 T cells of a myasthenia gravis patient and compositions for the treatment of myasthenia gravis containing the same as an effective ingredient, more precisely, recombinant acetylcholine receptor polypeptides deficient in B cell epitope, recombinant acetylcholine polypeptides in which two or more T cell epitopes are fused, a composition for the treatment of myasthenia gravis containing the above recombinant polypeptides as an effective ingredient and a treatment method for myasthenia gravis using the composition. The composition containing one or more recombinant polypeptides above can be effectively used as a myasthenia gravis specific therapeutic agent or immunomodulator without side effects.

2 Claims, 13 Drawing Sheets

Fig. 3

A. B-cell epitope Δ67-76

| | | | |
|---|---|---|---|
| Consensus | TTACAACCTAAA | | AAAAATTCACATTC |
| | <Pos = 326 | | |
| 4 Sequences | 330 340 350 360 370 380 | | |
| pThio-His-d67-76d129-145 | TTACAACCTAAA----------------------------AAAAATTCACATTC | | (SEQ ID NO:58) |
| pThio-His-d67-76d129-145 | TTACAACCTAAA----------------------------AAAAATTCACATTC | | (SEQ ID NO:58) |
| pThio-His-d67-76d129-145 | TTACAACCTAAA----------------------------AAAAATTCACATTC | | (SEQ ID NO:58) |
| pThio-His-d67-76d129-145 | TTACAACCTAAA----------------------------AAAAATTCACATTC | | (SEQ ID NO:58) |
| DNA_Human_ORI | TTACAACCTAAAATGGAATCCAGATGACTATGGCGGTGTGAAAAAATTCACATTC | | (SEQ ID NO:59) |

B. B-cell epitope Δ129-145

| | | | |
|---|---|---|---|
| Consensus | CTACTGT | | CTGGGC |
| | <Pos = 513 | | |
| 4 Sequences | 520 530 540 550 560 570 | | |
| pThio-His-d67-76d129-145 | CTACTGT--------------------------------------CTGGGC | | (SEQ ID NO:60) |
| pThio-His-d67-76d129-145 | CTACTGT--------------------------------------CTGGGC | | (SEQ ID NO:60) |
| pThio-His-d67-76d129-145 | CTACTGT--------------------------------------CTGGGC | | (SEQ ID NO:60) |
| pThio-His-d67-76d129-145 | CTACTGT--------------------------------------CTGGGC | | (SEQ ID NO:60) |
| Human AChR Alpa | CTACTGTGAGATCATCGTCACCCACTTTCCCTTTGATGAACAGAACTGCAGCATGAAGCTGGGC | | (SEQ ID NO:61) |

Fig. 4

```
tccgaacatgagacccgtctgtggcaaagctatttaaagactacagcagcgtggtgcggccagtggaagaccaccg
 S  E  H  E  T  R  L  V  A  K  L  F  K  D  Y  S  S  V  V  R  P  V  E  D  H  R ccaggtcgtggaggtcacgtgggcctgcagctgatacagctcatcaatgtggatgaagtaaatcagatcgtgacaa
 Q  V  V  E  V  T  V  G  L  Q  L  I  Q  L  I  N  V  D  E  V  N  Q  I  V  T  T ccaatgtgcgtctgaaacagcaatggtggattacaacctaaaatggaatccagatgactatggcggtgtgaaaaaa
 N  V  R  L  K  Q  Q  W  V  D  Y  N  L  K  W  N  P  D  D  Y  G  G  V  K  K attcacattcctcagaaaagatctgcagtacactggccacatcacgtggacacctccagccatctttaaagctgtg
 I  H  I  P  S  E  K  I  W  R  P  D  L  V  L  Y  N  N  A  D  G  D  F  A  I  V caagttcaccaaagtgctcctgcagtacactggccacatcacgtggacacctccagccatctttaaagctactgtg
 K  F  T  K  V  L  L  Q  Y  T  G  H  I  T  W  T  P  P  A  I  F  K  S  Y  C agatcatcgtcacccacttccctttgatgaacagaactgcagcatgaagctgggcacctgaacctacgacggctct
 I  I  V  T  H  F  P  F  D  E  Q  N  C  S  M  K  L  G  T  W  T  Y  D  G  S gtcgtggccatcaacccggaaagtgaccagccagacctgagcaacttcatggagagcggggagtgggtgatcaagga
 V  V  A  I  N  P  E  S  D  Q  P  D  L  S  N  F  M  E  S  G  E  W  V  I  K  E gtcccggggctgaagcactcctgacctattcctgtgcccgacatccctacctggacatcacctaccacttcg
 S  R  G  W  K  H  S  V  T  Y  S  C  C  P  D  T  P  Y  L  D  I  T  Y  H  F  V tcatgcagcgcctg    (SEQ ID NO:57)
 M  Q  R  L       (SEQ ID NO:56)
```

Fig. 8
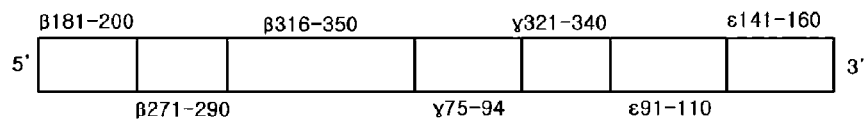
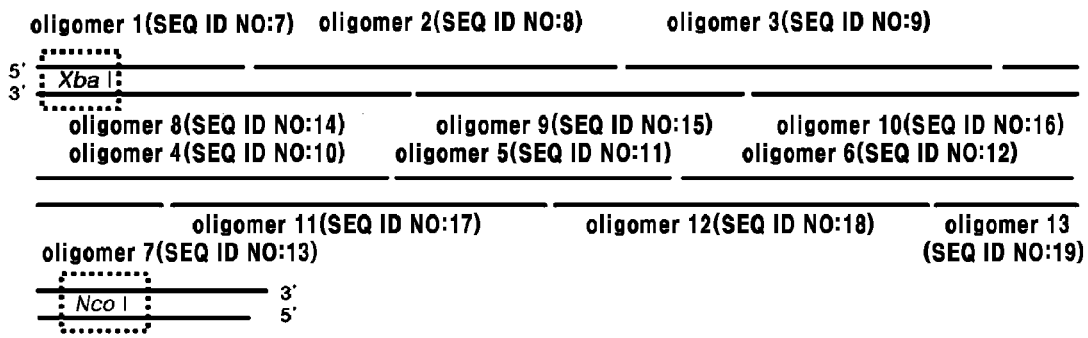
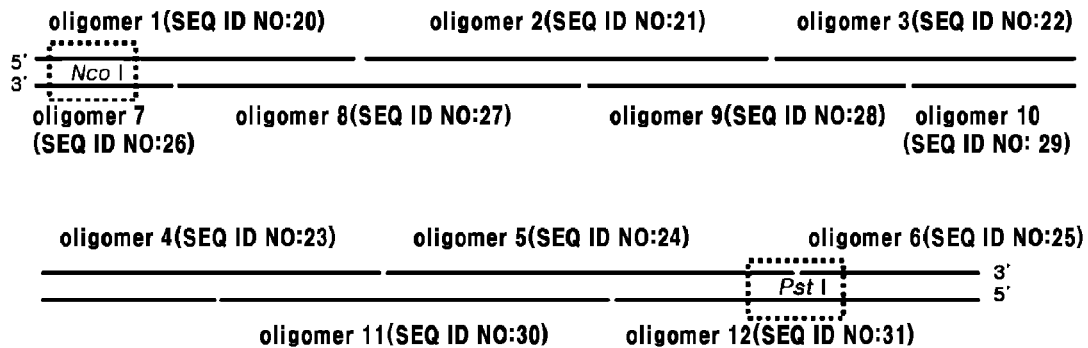

Fig. 12

| | | | α subunit[a] | |
|---|---|---|---|---|
| Region | Region | Region | Region | Region |
| α1-80 | α101-168 | α191-207 | α293-337 | α387-437 |
| α1-14 | α101-120 | α191-207 | α293-308 | α387-405 |
| α19-34 | α118-137 | | α304-322 | α403-421 |
| α32-51 | α135-154 | | α320-337 | α419-437 |
| α48-67 | α151-168 | | | |
| α63-80 | | | | |

| | | | β Subunit[b] | |
|---|---|---|---|---|
| Region | Region | Region | Region | Region |
| β16-50 | β181-200 | β271-290 | β316-350 | β361-425 |
| β16-35 | β181-200 | β271-290 | β316-335 | β361-380 |
| β31-50 | | | β331-350 | β376-395 |
| | | | | β391-410 |
| | | | | β406-425 |

| | | | γ Subunit[c] | | | | |
|---|---|---|---|---|---|---|---|
| Region | Region | Region | Region | Region | Region | Region | Region |
| γ30-49 | γ60-124 | γ135-154 | γ248-288 | γ297-355 | γ366-400 | γ411-430 | γ470-495 |
| γ30-49 | γ60-79 | γ135-154 | γ248-267 | γ297-312 | γ366-385 | γ411-430 | γ470-489 |
| | γ75-94 | | γ263-273 | γ306-325 | γ381-400 | | γ476-495 |
| | γ90-109 | | γ269-288 | γ321-340 | | | |
| | γ105-124 | | | γ336-355 | | | |

| | | | δ Subunit[d] | | |
|---|---|---|---|---|---|
| Region | Region | Region | Region | Region | Region |
| δ1-20 | δ61-80 | δ91-185 | δ196-290 | δ346-392 | δ461-496 |
| δ1-20 | δ61-80 | δ91-110 | δ196-215 | δ346-362 | δ461-480 |
| | | δ106-125 | δ213-230 | δ363-386 | δ476-496 |
| | | δ121-140 | δ226-245 | δ373-392 | |
| | | δ136-155 | δ241-260 | | |
| | | δ151-170 | δ256-275 | | |
| | | δ166-185 | δ271-290 | | |

| | | | ε Subunit[e] | | |
|---|---|---|---|---|---|
| Region | Region | Region | Region | Region | Region |
| ε51-70 | ε91-110 | ε121-170 | ε231-320 | ε351-370 | ε431-473 |
| ε51-70 | ε91-110 | ε121-140 | ε231-250 | 351-370 | ε431-450 |
| | | ε141-160 | ε241-260 | | ε431-470 |
| | | ε151-170 | ε261-280 | | ε461-473 |
| | | | ε281-300 | | |
| | | | ε291-310 | | |
| | | | ε301-320 | | |

[a] From references 39, 42 and 46.
[b] From references 43.
[c] From references 40 and 45.
[d] From references 40 and 44.
[e] From an unpublished study by Z. Y. Wang et al.

RECOMBINANT CHIMERIC ACETYLCHOLINE RECEPTORS AND THEIR DERIVATIVES RECOGNIZED BY CD4 T CELLS OF MYASTHENIC PATIENTS FOR THE TREATMENT OF MYASTHENIA GRAVIS

BACKGROUND OF THE INVENTION (a) Field of the Invention

The present invention relates to recombinant chimeric acetylcholine receptor polypeptides recognized by CD4 T cells of a myasthenia gravis patient and chimeric acetylcholine derivatives for the treatment of myasthenia gravis containing the same as an effective ingredient, more precisely, recombinant acetylcholine receptor polypeptides deficient in B cell epitopes, recombinant acetylcholine polypeptides in which two or more T cell epitopes are fused, a composition for the treatment of myasthenia gravis containing the above recombinant polypeptides as an effective ingredient and a treatment method for myasthenia gravis using the compositions.

(b) Description of the Related Art

Autoimmune disease is led by the immune response induced against self-components (proteins or cells) according to the loss of self-tolerance. T cells regulating immune response are matured in thymus, in which they are instructed to cause immune response by recognizing an antigen linked to their MHC (major histocompatibility complex). Basically, T cells can not respond to those cells that have their own antigens in their MHC, but from time to time, self-active T cells are generated to recognize an antigen complex produced by the combination of their MHC and the antigens therein. Autoimmune disease is not infectious but inherited. In some cases, autoimmune disease can be triggered or worsened by virus infection, aging, chromium poisoning, hormones and pregnancy.

Autoimmune disease is a chronic disease, whose cause has not been disclosed, yet. Studies on autoantigens have been underway. Most autoimmune diseases are closely related to the activities of T cells, B cells and antigen presenting cells. Approaches to treat such autoimmune diseases are largely outlined by following four methods; first, targeting a subject which is involved in the activity of an immune cell; second, regulating an antigen-specific immune response; third, reconstructing immune system by transplanting autologous or allogeneic stem cells; and fourth, transplanting an organ. Besides, to treat autoimmune diseases, conventional immunosuppressants have been widely used, which are exemplified by calcineurin inhibitors (cyclosporin, tacrolimus), antimetabolites (azathioprine, leflunomide, methotrexate, mycophenolate mofetil), antiproliferatives (sirolimus), monoclonal antibodies to T lymphocyte (basiliximab, daclizumab, muromonab-CD3) and anticytokines (anakinra, etanercept, infliximab). Recently, approximately more than 23 immunosuppressants are under clinical trial or ready for the trial (*Expert Opin Emerg Drugs.* 2003 May; 8(1):47-62). The gene therapy has recently been tried out to treat autoimmune diseases, for example, CD4+ T cells are infected with a vector specially designed to express cytokines (IL-4, IL-10, IL-12p40) having functions of immunoregulation, which are then amplified to be used as a cell therapy agent (*Autoimmun Rev.* 2002; 1(4):213-9); *Curr Opin Immunol.* 2001; 13(6):676-82). However, the above methods not only inhibit abnormal autoimmune responses but also suppress normal immune response to protect human body from an invading antigen, so that it might increase the chances of infectious diseases and other side effects including weakening the function of inhibiting tumor expression by immune cells.

Another attempt has been made to treat autoimmune disease. Oral administrations of autoimmune disease specific antigens have induced antigen-specific immune tolerance in various experimental autoimmune animal models. These are including following experimental autoimmune model systems; bovine/chicken collagen for the treatment of rheumatoid arthritis, myelin basic protein for the treatment of multiple sclerosis, insulin for the treatment of type-I diabetes and IRBP (interphotoreceptor retinoid-binding protein) for the treatment of autoimmune uveitis. However, the oral administration of these antigens was effective mainly in animal models but not in human clinical trials. There are still problems in the development of an oral immune regulator. The immune responses mediated by CD8 cells and B cells against orally administered proteins have not been considered.

In summary, for the development of safe and effective oral immunomodulator potential immunoactivator function of orally administered protein should be considered. For example, to develop oral immunomodulator targeting CD4 T cell immune responses, orally administered proteins should induce hypoimmune response to administered antigen-specific CD4+ T cells without stimulating immune responses mediated by antigen-specific B cells and CD8 cells.

Myasthenia gravis is one of chronic autoimmune diseases, which has the incidence of 1/5,000-10,000. Currently antigen-specific therapeutic agent for myasthenia gravis has not been developed, yet. Myasthenia gravis is developed when the normal binding acetylcholine to acetylcholine receptor (referred as "AChR" hereinafter) is interrupted in neuromuscular junction. In Myasthenia gravis anti-AChR antibody to self-AChR acts as an inhibitor of signal transduction in the neuromuscular junction. In fact, approximately 80% of myasthenia gravis patients have been reported to harbor antibodies responding to AChR. The antibody responding to AChR can be a direct cause of the disease and the generation of the antibody is essentially involved in the action of T cells. Namely generation of AChR-specific antibody is depending on AChR-reactive T cell. Therefore, any substance that can incapacitate AChR-specific T cells or B cells can be used for the treatment of myasthenia gravis. For the treatment of myasthenia gravis, non-specific treatment methods (immune inhibitor, intravenously injectable immunoglobulin, and plasmapheresis) and acetylcholine esterase inhibitor known as mestinon are in use, and the market for them is growing every year. Nevertheless, the therapeutic agents in use have side effects and show limited effects.

AChR is composed of two $\alpha$, $\beta$, $\gamma$ and $\delta$ ($\epsilon$) chains. Most autoimmune response related T cell and B cell antigens localize in the $\alpha$ chain (see FIG. 1), particularly in the extracellular domain of the $\alpha$ chain, and B cell epitope known as MIR (main immunogenic region) and various AChR-reactive epitopes antigens are also localized in non-alpha chains.

US Patent Publication No. 2002-0081652 describes the production of a polypeptide derived from human AChR $\alpha$ subunit. But, the polypeptide still harbors the B cell epitopes that could be recognized by auto-AChR reactive B-cell receptors in myasthenia gravis. This could be harmful when B-cell epitope-containing human AChR $\alpha$ subunit is administered into a myasthenia gravis patient or animal since AChR-reactive B-cell receptors could recognizes B cells, thereof to activate AChR-reactive B cells as well as T cells. Indeed when B-cell epitope containing human AChR $\alpha$ subunit was administered in acute state of myathenic rats it exacerbated myasthenia by stimulating AChR-reactive T cells as well as B cells (Im et al., *J Immunol.*, 165: 3599-3605, 2000).

The present inventors produced a polypeptide by inserting P3A sequence which is composed of 25 amino acids expressed only in some of acetylcholine receptors into the region between the $58^{th}$ and the $59^{th}$ amino acids among $1^{st}$-$205^{th}$ amino acids of human AChR α subunit, and then confirmed that the produced polypeptide characteristically has the structure reducing antigenicity of B cell epitope against myasthenia gravis. The present inventors further induced immune tolerance against an autoantigen by the oral administration of the produced polypeptide to an animal model with myasthenia gravis (Im et al., *J Clin. Invest.*, 165: 3599-3605, 2000). And also, the present inventors made an attempt to treat myasthenia gravis by the intranasal administration of the produced polypeptide to an animal model with myasthenia gravis (Im et al., *J Neuroimmunol.*, 111(1-2) :161-168, 2000).

SUMMARY OF THE INVENTION

It is an object of the present invention to provide recombinant polypeptides of acetylcholine receptor (referred as "AChR" hereinafter) deficient in B cell epitopes, the genes thereof and polynucleotides encoding the same.

It is another object of the present invention to provide an expression vector containing a polynucleotide encoding the above polypeptide and a transformant transformed with the vector.

It is another object of the present invention to provide recombinant chimeric AChR polypeptides in which two or more T cell epitopes are linked and a gene thereof and polynucleotides encoding the same.

It is another object of the present invention to provide an expression vector harboring polynucleotides encoding the above polypeptide and an *E. coli* transformants transfected with the vector.

It is another object of the present invention to provide a therapeutic agent for myasthenia gravis containing AChR recombinant polypeptide in which B cell epitopes are deleted and/or AChR recombinant polypeptides in which T cell epitopes of myathenic patients are linked.

It is a further object of the present invention to provide a method for the treatment of myasthenia gravis containing the step of administrating the effective dose of AChR recombinant polypeptide in which B cell epitope is deleted and AChR recombinant polypeptide in which T cell epitopes are fused to a mammalian.

BRIEF DESCRIPTION OF THE DRAWINGS

FIG. 2A-A: deficiency in amino acid sequence between $67^{th}$ and $76^{th}$, confirmed by electrophoresis;

Figure 1:
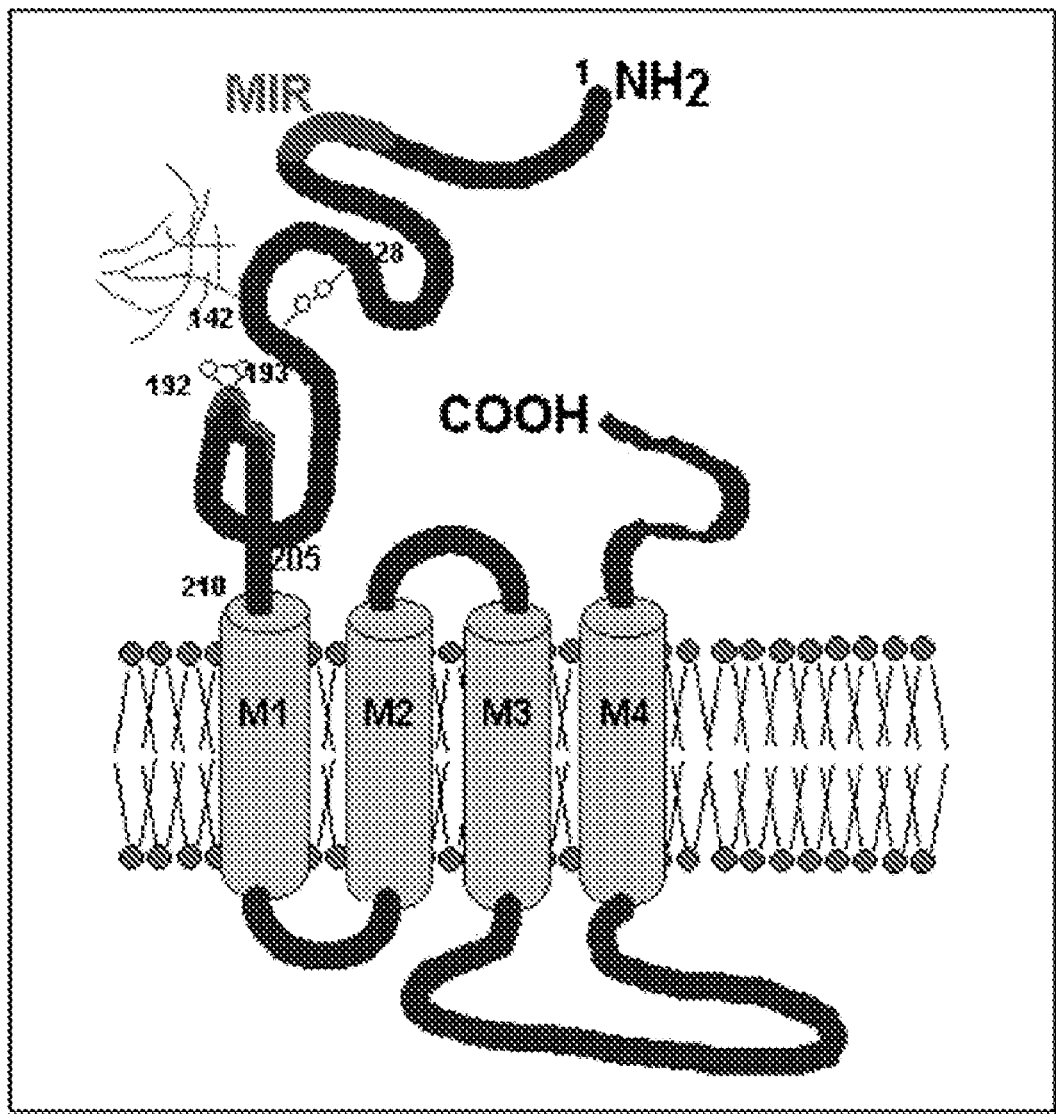
FIG. 1 is a schematic diagram showing the structure of α subunit of human acetylcholine receptor (referred as "hAChR" hereinafter).
Figure 2A:
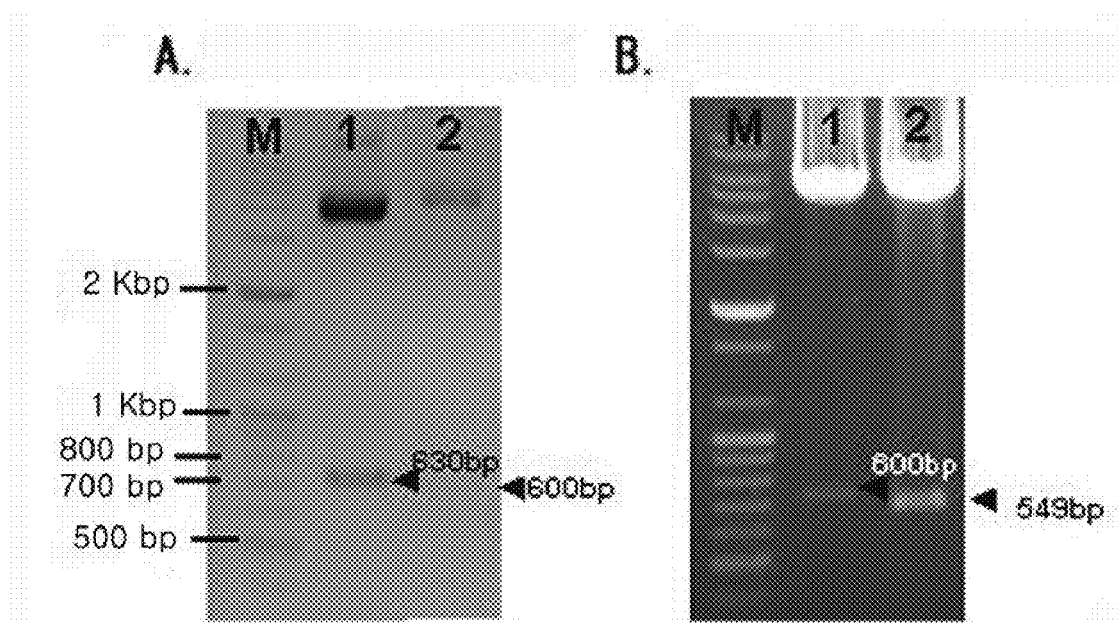
FIG. 2A is deficiency in amino acid sequence between $67^{th}$-$76^{th}$, $129^{th}$-$145^{th}$, confirmed by electrophoresis.
Figure 2B:
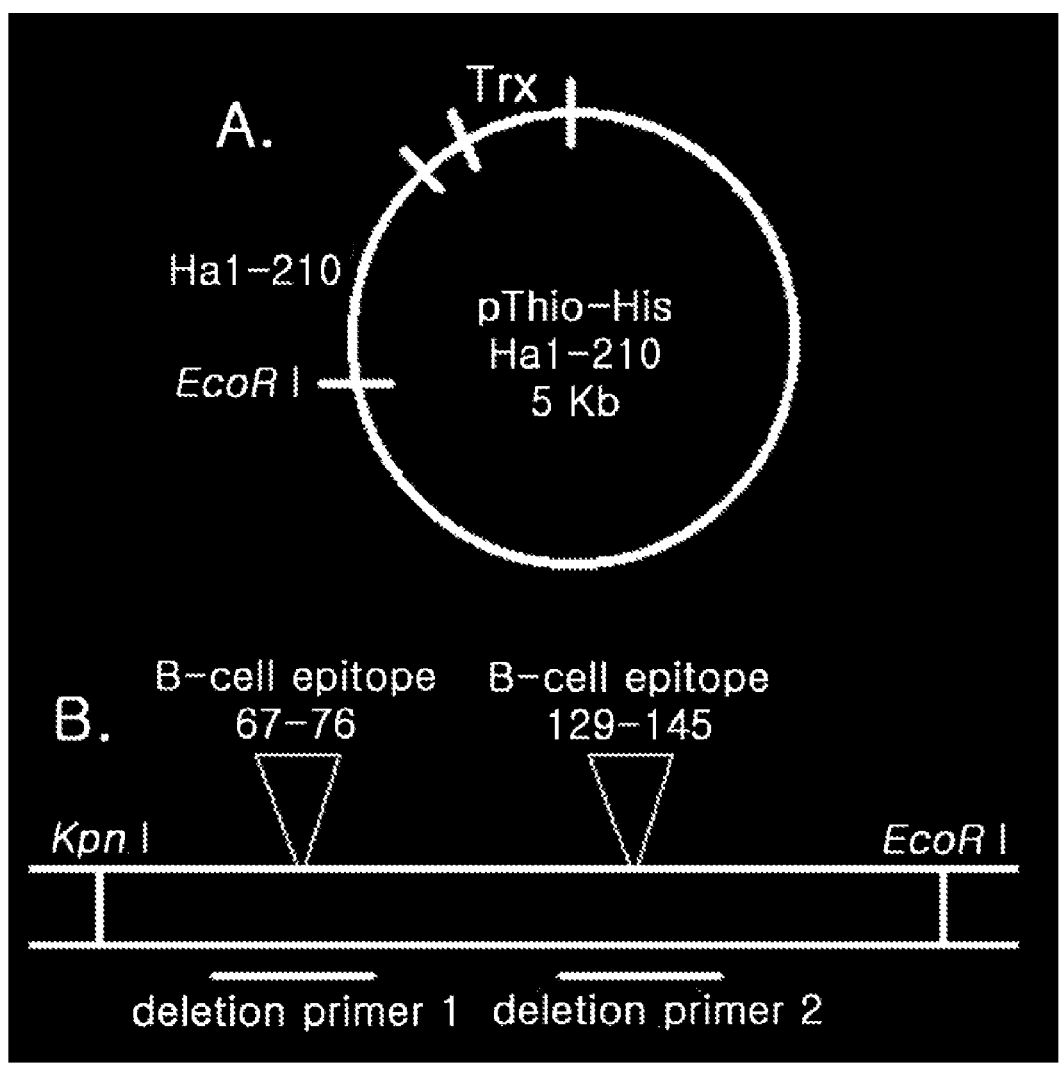
FIG. 2 is a diagram illustrating the sequence deficiency between $67_{th}$-$76^{th}$ and $129^{th}$-$145^{th}$ amino acid of hAChR α subunit.

M: marker;

1: pThioHis-Ha1-210;

2: pThioHis-Ha1-210Δ67-76;

FIG. 2A-B: deficiency in amino acid sequence between $129^{th}$ and $145^{th}$, confirmed by electrophoresis;

M: marker;

1: pThioHis-Ha1-210Δ67-76;

2: pThioHis-Ha1-210Δ67-76Δ129-145;

FIG. 2B is diagram illustrating the sequence deficiency between $67^{th}$-$76^{th}$ and $129^{th}$-$145^{th}$ amino acid of hAChR α subunit:

FIG. 2B-C: plasmid map of pThioHis-Hal-210; and

FIG. 2B-D: deficiency in amino acid sequence between $67^{th}$-$76^{th}$ and $129^{th}$-$145^{th}$.

FIG. 3 is a diagram showing the comparison of nucleotide sequences between hAChR α subunit and the deletion form of hAChR α subunit:

A: deficiency in amino acid sequence between $67^{th}$ and $76^{th}$ amino acid of B cell epitope;

B: deficiency in amino acid sequence between $129^{th}$ and $145^{th}$ amino acid of B cell epitope; and Straight line: sequence-corresponding region.

FIG. 4 is a diagram showing the comparison of amino acid sequences between hAChR α subunit and the deletion form of hAChR α subunit:

Straight line: the location of a deleted primer; and

Square box: the location where B cell epitope is deleted.

Figure 5:
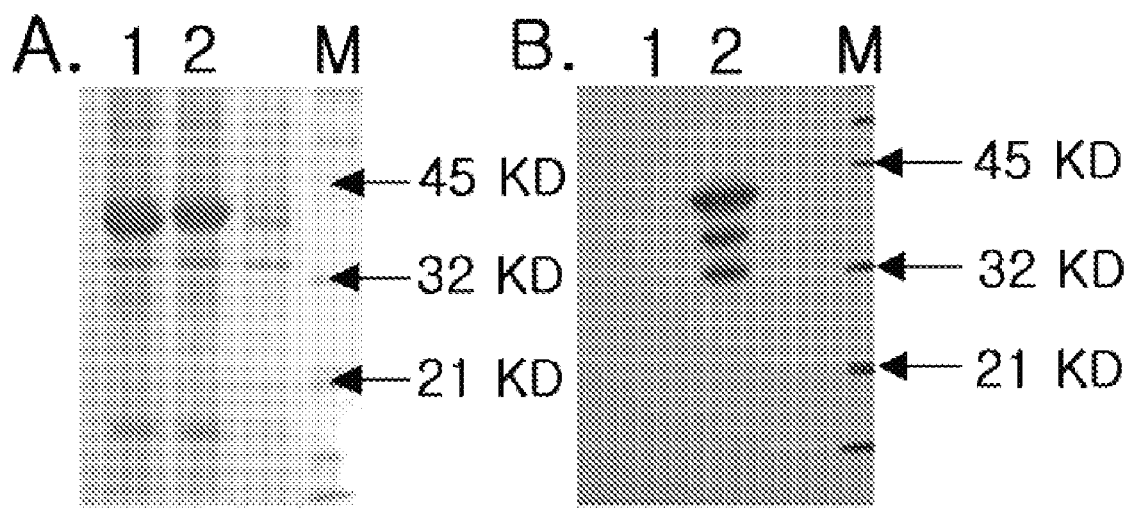

FIG. 5 is an electrophoresis photograph illustrating the expression of hAChR α subunit, B cell epitope deleted polypeptide in *E. coli:*

A: SDS-PAGE;

B: western blot using a monoclonal antibody (mAB 198) having an affinity for hAChR α subunit MIR (maim immunogenic region);

1: Trx-Ha1-210 Δ67-76 Δ129-145;

2: Trx-Ha1-210; and

M: marker.

Figure 6:
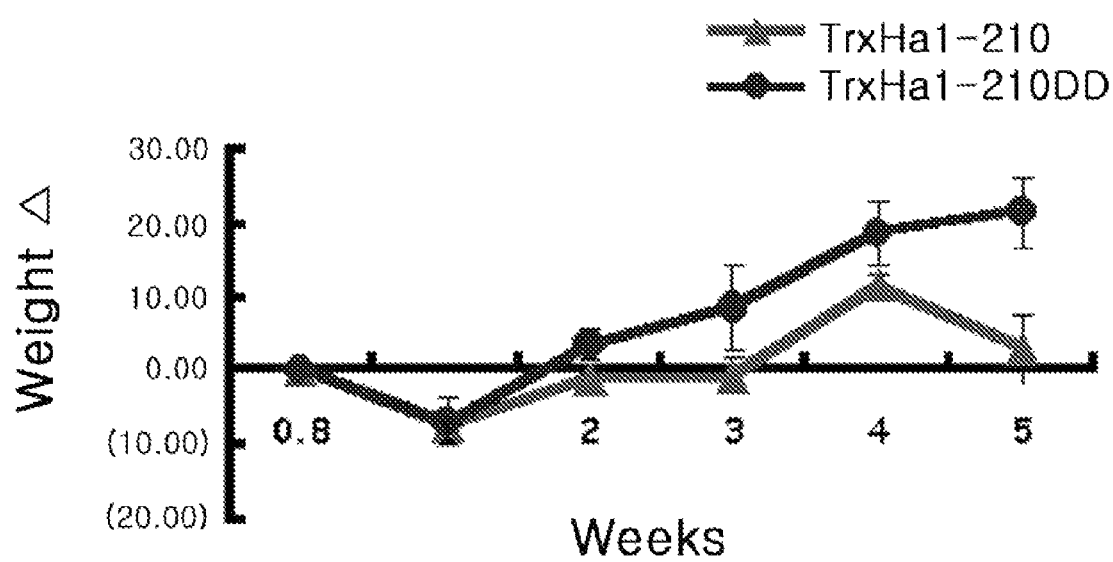

FIG. 6 is a graph illustrating the weight changes in an animal model according to the oral administration of the polypeptide composition with the deletion of B cell epitope of the hAChR α subunit:

TrxHa1-210: hAChR 1-210; and

TrxHa1-210ΔΔ: B cell epitope is deleted between $67^{th}$-$76^{th}$ and $129^{th}$-$145^{th}$ in hAChR 1-210.

Figure 7:
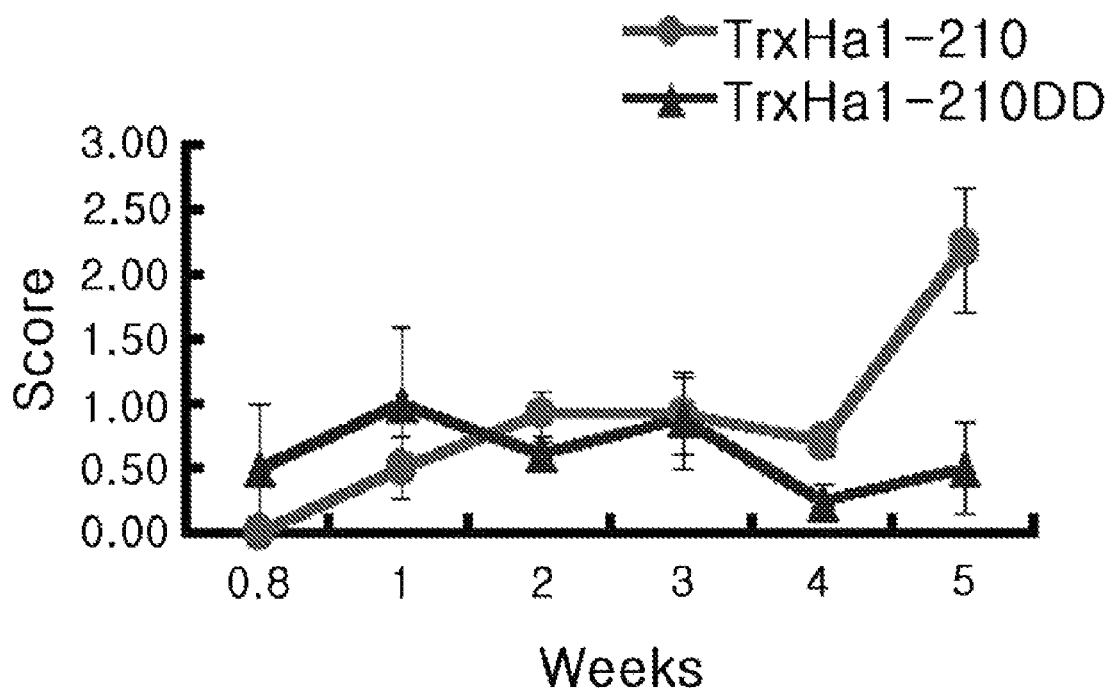

FIG. 7 is a graph illustrating clinical scores obtained after the oral administration of the polypeptide composition with the deletion of B cell epitope of the hAChR α subunit to an animal model:

TrxHa1-210: hAChR 1-210; and

TrxHa1-210ΔΔ: B cell epitope is deleted between $67^{th}$-$76^{th}$ and $129^{th}$-$145^{th}$ in hAChR 1-210.

FIG. 8 is a diagram showing the structures of CD4+ cell epitopes of hAChR β, γ and ε subunits and oligomers thereof.

Figure 9:
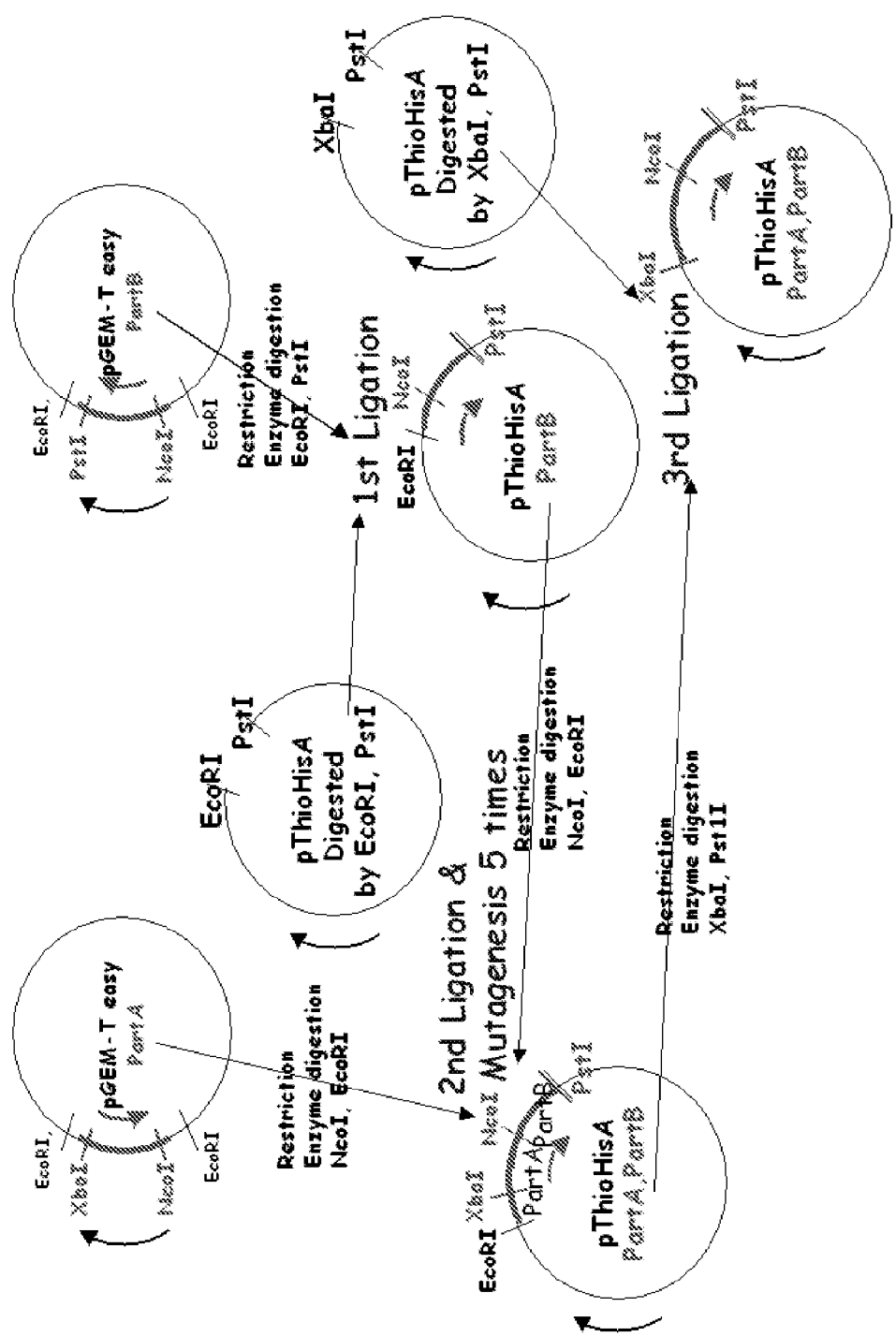

FIG. 9 is a schematic diagram illustrating the cloning of CD4+ T cell epitopes of hAChR β, γ and ε subunit genes.

Figure 10:
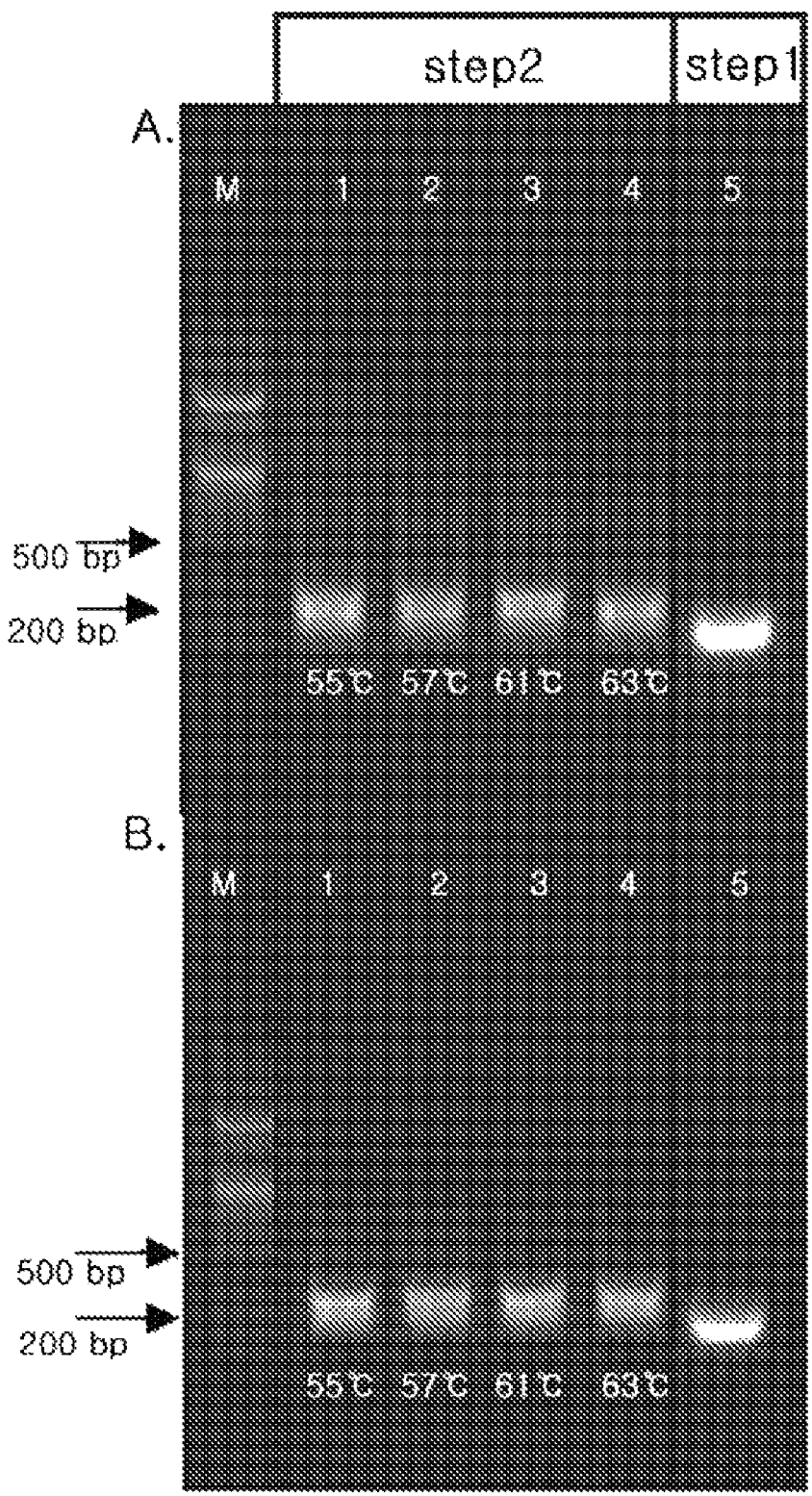

FIG. 10 is an electrophoresis photograph illustrating the formation of a plasmid containing part A and part B composed of the combinations of T cell epitopes among hAChR β, γ and ε subunit chains.

Figure 11:
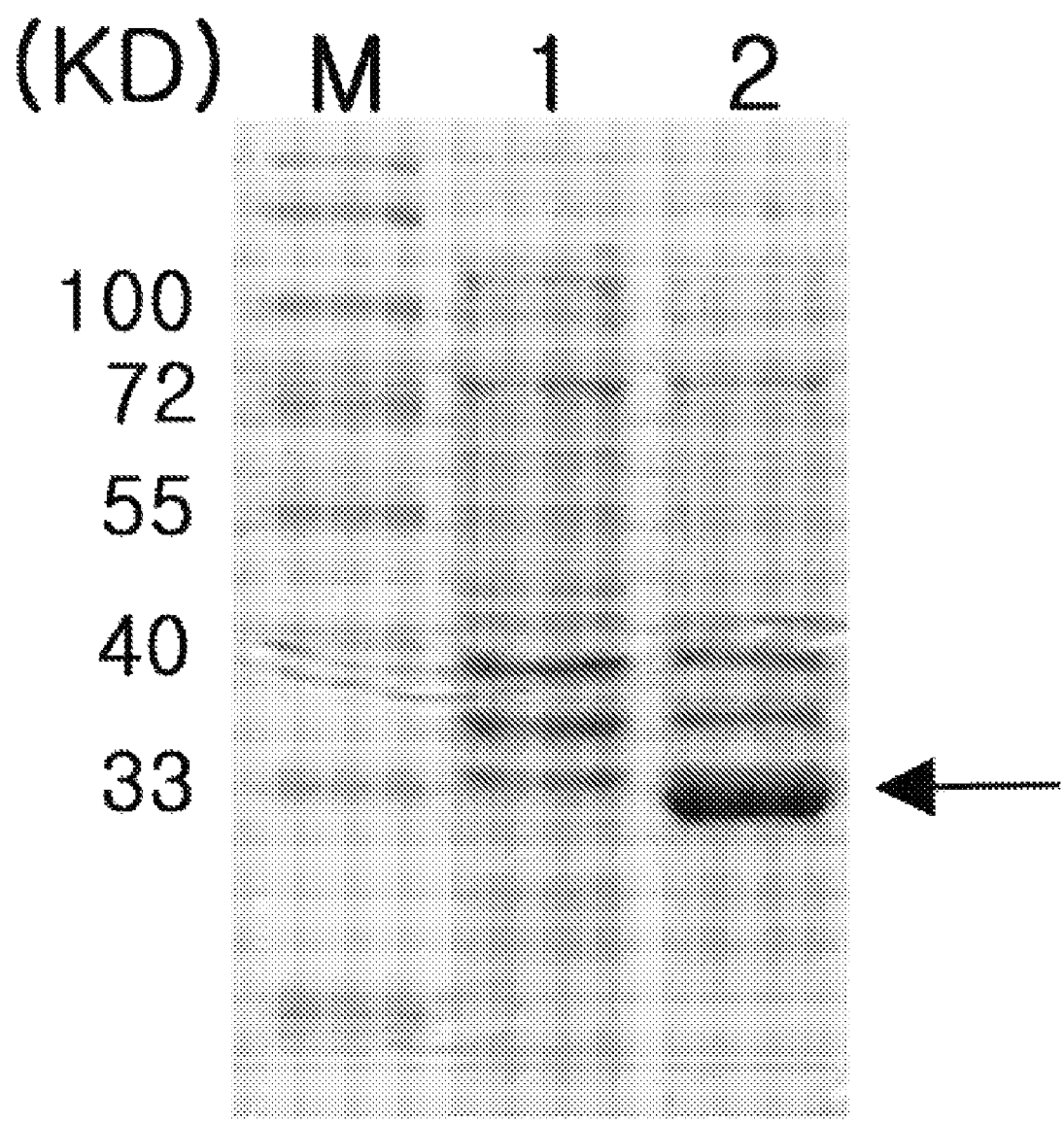

FIG. 11 is a SDS-PAGE photograph illustrating the expression of *E. coli* strain transformed with an expression vector harboring hAChR CD4+ cell epitope:

M: marker;
1: IPTG untreated;
2: IPTG treated; and
Arrow: Trx:T cell epitope peptide.

FIG. 12 is a diagram showing CD4+ T lymphocyte epitope of hAChR subunit of a myasthenia gravis patient.

DETAILED DESCRIPTION OF THE PREFERRED EMBODIMENTS

To achieve the above objects, the present invention provides recombinant polypeptides of acetylcholine receptor (referred as "AChR" hereinafter) deficient in B cell epitope, the genes thereof and polynucleotides encoding the same.

The present invention also provides an expression vector containing a polynucleotide encoding the above polypeptide and a transformant transformed with the vector.

The present invention also provides an AChR recombinant polypeptide in which two or more T cell epitopes are fused and a gene thereof and a polynucleotide encoding the same.

The present invention also provides an expression vector harboring a polynucleotide encoding the above polypeptide and an *E. coli* transformant transfected with the vector.

The present invention also provides a therapeutic agent for myasthenia gravis containing AChR recombinant polypeptide in which B cell epitope is deleted and/or AChR recombinant polypeptide in which T cell epitopes are fused.

The present invention further provides a method for the treatment of myasthenia gravis containing the step of administrating the effective dose of AChR recombinant polypeptide in which B cell epitope is deleted and AChR recombinant polypeptide in which T cell epitopes are fused to a mammalian.

Hereinafter, the present invention is described in detail.

The present invention provides recombinant polypeptides of human acetylcholine receptor (referred as "hAChR" hereinafter) deficient in B cell epitope. The hAChR is composed of two α, β, γ and δ (ε) chains. However, most B lymphocyte antigens involved in autoimmune responses localize in the α chain, particularly the extracellular domain of the α chain. Therefore, the hAChR fragment is deficient in B cell epitope in amino acid sequence corresponding to the extracellular domain of the α chain, which is preferably represented by SEQ. ID. NO: 32, NO: 33 or NO: 34 and more preferably is represented by SEQ. ID. NO: 34.

In the present invention, a recombinant hAChR polypeptide lacking B cell epitope was amplified by polymerase chain reaction (referred as "PCR" hereinafter) using hAChR gene derived from cDNA of mRNA of TE671 cell line as a template and a set of primers represented by SEQ. ID. NO: 1 and NO: 2. The PCR product was inserted into pThio-HisA vector (Invitrogen, USA), which was then named pThio-HisHa1-210. To delete $67^{th}$-$76^{th}$ and $129^{th}$-$145^{th}$ amino acids, on which B cell epitope resides, PCR was performed again to prepare a deletion form by using pThio-HisHa1-210 as a template with the deletion primer 1 represented by SEQ. ID. NO: 3 and NO: 4 and the deletion primer 2 represented by SEQ. ID. NO: 5 and NO: 6 (see FIG. 2). The prepared polypeptide was orally administered together with hAChR α subunit polypeptide to a myasthenia gravis animal model and the weight changes of the animal were observed, followed by clinical scoring. The administration of B cell epitope deleted hAChR α subunit polypeptide relieved weight-loss, compared with hAChR α subunit polypeptide (see FIG. 6). From the results of clinical scoring, hAChR polypeptide showed worse clinical scores than B cell epitope deleted hAChR polypeptide (see FIG. 7).

The present invention also provides a polynucleotide encoding the polypeptide of the invention. There are various codons which are encoding the same amino acid owing to codon degeneracy. So, even if genes are encoding the same amino acid, they might have different nucleotide sequences. And the gene of the invention is preferably represented by SEQ. ID. NO: 35, NO: 36 or NO: 37.

The present invention further provides an expression vector harboring the polynucleotide and a transformant prepared by inserting the expression vector into a host cell. The biochemically active polypeptide or the fragment thereof can be separated or produced by cloning the polynucleotide which also enables the expression of a target gene in an appropriate host cell. To do so, a DNA molecule (polynucleotide) is inserted into a plasmid or a virus vector for the efficient self-replication in a selected host cell. The expression vector thereby can be used for the transformation of such host cells as eukaryotes and prokaryotes. The expression vector available for the transformation of prokaryotes is exemplified by a plasmid such as pThio-HisA (Invitrogen, USA) which is reproductive in *E. coli* and a bacteriophage vector such as λgt11, λgt18-23 and M13 originated vector, but not always limited thereto. The expression vector for the transformation of eukaryotes is exemplified by retrovirus and vaccinia virus, but not always limited thereto, either. To transform a host cell with the expression vector containing the nucleotide of the invention, one of the following methods which are well-known to those in the art can be selected; transformation, transfection, lipofection, conjugation, protoplast fusion, electroporation, calcium phosphate precipitation and direct microinjection. It is preferred to select a host cell from a group consisting of *E. coli*, a yeast such as *Saccharomyces cerevisiae*, an insect cell line such as Sf9 (*Spodoptera frugiperda*) and a mammalian cell line such as CHO (Chinese hamster ovary), but not always limited thereto. Prokaryotic cells are appropriated host cells for the production of the polypeptide of the invention. Since a non-native polypeptide has been proved to be more successful than a native polypeptide, it is expected that the polypeptide expressed in a prokaryotic system will be more successful than that in an eukaryotic system.

The present invention also provides a recombinant polypeptide with the fusion of two or more T cell epitopes of AChR. The present inventors tried to induce immune tolerance by using the T cell epitope fused recombinant polypeptide. Cytoplasmic site of AChR is normally in the inside of a cell so that it can be protected from any antibody response. But, as a disease progresses, cell membrane can be destroyed by the reaction of antibody and complements, and thus immune response can reach the inside of a cell through cell membrane. Thus, in the present invention, T cell epitope includes not only the one in α chain but also T cell epitopes in cytoplasmic site and amino terminal region. It is preferred to select the T cell epitope from a group consisting of the epitope having an amino acid sequence represented by SEQ. ID. NO: 38 (α 48-67); the epitope having an amino acid sequence represented by SEQ. ID. NO: 39 (α 101-120); the epitope having an amino acid sequence represented by SEQ. ID. NO: 40 (α 118-137); the epitope having an amino acid sequence represented by SEQ. ID. NO: 41 (α 304-328); the epitope having an amino acid sequence represented by SEQ. ID. NO: 42 (α 403-421); the epitope having an amino acid sequence represented by SEQ. ID. NO: 43 (α 419-437); the epitope having an amino acid sequence represented by SEQ. ID. NO: 44 (β 181-210); the epitope having an amino acid sequence represented by SEQ. ID. NO: 45 (β 271-290); the epitope having an amino acid sequence represented by SEQ. ID. NO: 46 (β 316-350); the epitope having an amino acid sequence represented by SEQ. ID. NO: 47 (γ 75-94); the epitope having an amino acid sequence represented by SEQ. ID. NO: 48 (γ 321-340); the epitope having an amino acid sequence represented by SEQ. ID. NO: 49 (ε 91-110); and the epitope having an amino acid sequence represented by SEQ. ID. NO: 50 (ε 141-160). Any recombinant polypeptide with the fusion of two or more epitopes selected from the above can be included in the criteria of the present invention, but a polypeptide with the fusion of 7 different epitopes and having the amino acid sequence represented by SEQ. ID. NO: 51 is preferred. A polypeptide with the fusion of all the 13 epitopes and having the amino acid sequence represented by SEQ. ID. NO: 53 is more preferred. At this time, the arrangement or the order of those T cell epitopes does not matter for the fusion.

To provide a polypeptide with the fusion of T cell epitopes of hAChR β, γ and ε chains, the present inventors designed an active site responding to CD4+ T cells to be composed of part A comprising 13 oligomers represented by SEQ. ID. NO: 7-NO: 19 and part B comprising 12 oligomers represented by SEQ. ID. NO: 20-NO: 31, based on the CD4+ T cell active site for each subunit of human acetylcholine of a myasthenia gravis patient. The single-stranded oligomer of part A or part B was synthesized by using Pfu, which was inserted into pGEM-T vector and named as pGEM-T easy Part A and pGEM-T easy Part B, respectively. Then, part A and part B were inserted together into pThio-HisA vector by using a restriction enzyme, which was named pThio-HisA-PartA-PartB. E. coli strain Top10 was transformed with the pThio-HisA-PartA-PartB, followed by confirmation of the transformation by SDS-PAGE (see FIG. 11).

The present invention provides a polynucleotide encoding the polypeptide of the invention, and the polynucleotide is preferably represented by SEQ. ID. NO: 52 or NO: 54. The present invention also provides an expression vector with the insertion of the polynucleotide and a transformant produced by inserting the expression vector to a host cell. The biochemically active polypeptide or the fragment thereof can be separated or produced by cloning the polynucleotide which also enables the expression of a target gene in an appropriate host cell. To do so, a DNA molecule (polynucleotide) is inserted into a plasmid or a virus vector for the efficient self-replication in a selected host cell. The expression vector thereby can be used for the transformation of such host cells as eukaryotes and prokaryotes. The expression vector available for the transformation of prokaryotes is exemplified by a plasmid such as pThio-HisA (Invitrogen, USA) which is reproductive in E. coli and a bacteriophage vector such as λgt11, λgt18-23 and M13 originated vector, but not always limited thereto. The expression vector for the transformation of eukaryotes is exemplified by retrovirus and vaccinia virus, but not always limited thereto, either. To transform a host cell with the expression vector containing the nucleotide of the invention, one of the following methods which are well-known to those in the art can be selected; transformation, transfection, lipofection, conjugation, protoplast fusion, electroporation, calcium phosphate precipitation and direct microinjection. It is preferred to select a host cell from groups consisting of E. coli, a yeast such as Saccharomyces cerevisiae, an insect cell line such as Sf9 (Spodoptera frugiperda) and a mammalian cell line such as CHO (Chinese hamster ovary), but not always limited thereto. Prokaryotic cells are appropriated host cells for the production of the polypeptide of the invention. Since a non-native polypeptide has been proved to be more successful than a native polypeptide, it is expected that the polypeptide expressed in a prokaryotic system will be more successful than that in an eukaryotic system.

The present invention provides a therapeutic agent for myasthenia gravis containing a recombinant polypeptide of hAChR fragment lacking myasthenia gravis specific recombinant B cell epitope and/or a recombinant polypeptide with the fusion of two or more T cell epitopes of hAChR as an effective ingredient.

The therapeutic agent of the invention can additionally include a modified polypeptide represented by SEQ. ID. NO: 55.

A therapeutic composition of the invention includes the above effective ingredient by 0.0001-50 weight % for the total weight.

The therapeutic composition of the present invention can also include, in addition to the above-mentioned effective ingredients, one or more pharmaceutically acceptable carriers for the administration. Pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following the method represented in Remington's Pharmaceutical Science (the newest edition), Mack Publishing Company, Easton Pa.

The therapeutic composition of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of the composition is 0.3~30 mg/kg per day, and preferably 0.5~10 mg/kg per day. Administration frequency is once a day or preferably a few times a day.

The therapeutic composition of the present invention can be administered singly or treated along with surgical operation, hormone therapy, chemotherapy and biological reaction regulator, to prevent and treat myasthenia gravis.

The present invention provides a method for the treatment of myasthenia gravis containing the step of administrating the effective dose of AChR recombinant polypeptide in which B cell epitope is deleted and AChR recombinant polypeptide in which T cell epitope is fused to a mammalian.

According to the conventional method, non-specific immunosuppressants such as steroid, azathioprine and cyclosporine are used for the treatment of myasthenia gravis. On the contrary, according to the method of the invention, myasthenia gravis specific immune cells are targeted, indicating that immune system is not weakened during the treatment of myasthenia gravis. The recombinant polypeptide of the invention is preferably selected from a group consisting of the polypeptide represented by SEQ. ID. NO: 32-NO: 34; the polypeptide represented by SEQ. ID. NO: 51 or NO: 53; and the polypeptide represented by SEQ. ID. NO: 55. And the therapeutic agent for myasthenia gravis is preferably administered through the nasal cavity or oral cavity.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Synthesis of Recombinant Construct (pThio-His Hα1-210Δ67-76, Δ129-145) DNA with the Deletion of B Cell Epitopes of Human Acetylcholine Receptor (hAChR) α Subunit (Hα1-210)

Human acetylcholine receptor (hAChR) α subunit (Hα1-210) gene derived from TE671 cell line was amplified by polymerase chain reaction (PCR) using a primer set represented by SEQ. ID. NO: 1 and NO: 2. PCR was performed as follows; denaturation at 95° C. for 60 seconds, annealing at 60° C. for 60 seconds, polymerization at 72° C. for 60 seconds, 30 cycles from denaturation to polymerization. 50 µg of the amplified DNA fragment was digested with 10 unit of each restriction enzyme Kpa I and EcoR I for 3 hours at 37° C., and then 50 µg of pThio-HisA vector (Invitrogen, USA), 1 unit of ligase and ligation buffer were reacted together for 10 hours at 16° C., followed by insertion. The product was named "pThio-HisHα1-210". 50 ng of pThio-HisAHα1-210 plasmid DNA containing the nucleotide sequence of hAChR α subunit, 20 pmol of deletion primer 1 represented by SEQ. ID. NO: 3 and NO: 4 and 2.5 unit of Pfu DNA polymerase (Bioneer, Korea) were mixed in 1 µl of dNTP, to which distilled water was added until the final volume was made as 50 µl, followed by reaction through 18 times of PCR cycles performed at 95° C. for 30 seconds, at 55° C. for 60 seconds and at 68° C. for 300 seconds. Then, 0.5 µl of restriction enzyme DPN I (NEB, USA) was added thereto, followed by further reaction for 10 hours at 37° C. The reactant was mixed with 20 pmol of deletion primer 2 represented by SEQ. ID. NO: 5 and NO: 6 and 2.5 unit of Pfu DNA polymerase (Bioneer, Korea) in 1 µl of dNTP, to which distilled water was added to make the total volume 50 µl. PCR was performed as follows; at 95° C. for 30 seconds, at 55° C. for 60 seconds, at 68° C. for 300 seconds (18 cycles). 0.5 µl of restriction enzyme KPN I (NEB, USA) was added thereto, followed by further reaction for 10 hours at 37° C. 2 µl of the final reaction solution was reacted with *E. coli* DH5α for 30 seconds at 42° C., which stood at 4° C. for 10 minutes thereafter. The mixture was smeared on an ampicillin containing medium and transformed *E. coli* cells were selected. The selected cells were cultured at 37° C. and a target plasmid lacking B cell epitope was separated by using Plasmid SV mini kit (GENEALL, Korea), which was named "pThio-HisHα1-210Δ67-76Δ129-145" (FIG. 2). Sequencing of the DNA was performed, so that the nucleotide sequences before and after the deletion were compared (FIG. 3). In addition, the location of B cell epitope and the structure of the deleted polypeptide were also examined (FIG. 4). As a result, the human acetylcholine receptor α subunit amino acid sequence was identified as the one represented by SEQ. ID. NO: 34.

Example 2

Synthesis of a Recombinant Polypeptide with the Deletion of B Cell Epitopes of hAChR α Subunit (Hα1-210) and Confirmation of the Deletion of B Cell Epitope 50 ng of pThio-HisAHα1-210Δ67-76Δ129-145 DNA prepared in Example 1 was reacted with 50 µl of *E. coli* Top 10 for 30 seconds at 42° C., which stood for 10 minutes thereafter. The reaction solution was placed in an ampicillin containing medium, followed by the selection of transformed *E. coli* cells. The selected *E. coli* cells were cultured in 5 ml LB medium for 10 hours at 37° C. and the culture solution was inoculated into 1 l LB medium, followed by further culture for 3 hours at 37° C. 1 mM of IPTG was added to the culture solution, followed by culture for four more hours. Centrifugation was performed with 10,000×g to separate *E. coli* cells from the culture solution. The isolated *E. coli* cells were washed twice with 50 mM Tris buffer and the cells were homogenized with a sonicator. The homogenized *E. coli* cells were diluted in 50 mM Tris buffer, followed by centrifugation at 10,000×g to remove the supernatant. Then, the precipitate was dissolved in 9 M urea solution, followed by centrifugation at 20,000×g for one hour. The supernatant was transferred onto the dialysis membrane, followed by dialysis with 50 mM Tris buffer 5 times every three hour. Centrifugation was performed at 20,000×g and as a result, a target polypeptide was obtained from the supernatant, which was named "TrxHα1-210Δ67-76Δ129-145". The polypeptide was electrophoresed on 12% SDS PAGE gel with 80 V for 2 hours and then transferred onto a nitrocellulose membrane (Biored, USA), followed by western blotting. After the transfer, the nitrocellulose membrane was soaked in a PBS solution containing 5% skim milk at room temperature for one hour to block the polypeptide-not-transferred regions. Western blotting was performed by using a monoclonal antibody (mAb 198, produced by Dr. Socrates Tzartos, Greece) having an affinity for MIR (main immunogenic region, Hα1-210 67-76) of AChR α chain. The membrane was reacted in PBS buffer containing the monoclonal antibody (mAb 198) for 90 minutes, followed by washing with PBS three times. Then, the membrane was treated with anti-mouse IgG-HRP (Sigma, USA) containing PBS for 60 minutes, followed by washing with PBS three times. The membrane was then reacted with ECL kit (Amersham Biosciences, UK) for one minute and then exposed on X-ray film.

From the SDS-PAGE, it was confirmed that Trx-Hα1-210Δ67-76Δ129-145 with the deletion of B cell epitope showed lower protein expression than Trx-Hα1-210 (see FIG. 5A). Also, from the Western blot analysis using the monoclonal antibody (mAb 198) having an affinity for MIR (main immunogenic region 67-76) of hAChR α subunit, it was confirmed that Trx-Hα1-210Δ67-76Δ129-145 had the deletion of B cell epitope (FIG. 5B).

Example 3

Examination of Weight Changes and Clinical Score after Oral Administration of Polypeptides TrxHα1-210, TrxHα1-210Δ67-76Δ129-145 in Experimental Autoimmune Myasthenia Gravis 45 µg of *Torpedo californica* AChR was mixed with CFA (Complete Freund Adjuvant), which was injected rear pads of a rat at 6-7 weeks to induce immunization. From one week after the immunization with *Torpedo californica* AChR, 600 µg of each TrxHα1-210 and TrxHα1-210Δ67-76Δ129-145 were orally administered to 6 and 5 rats, respectively, by using orogastric tube (Fisher, USA) two times per week. Weight changes were measured and clinical scoring was performed once a week. To determined clinical score, the scores measured by two different observers by using double blind method were averaged. Score 0 indicates no symptoms, score 1 indicates a faint fatigue and a weak grip of a rat, score 2 indicates a slight weight loss and gibbosity, score 3 indicates a severe weight loss and trembling and score 4 indicates death.

The results of the experiment are shown in the below table.

TABLE 1

Weight changes after oral administration of hAChR α subunit lacking B cell epitope

| | Week | | | | | |
|---|---|---|---|---|---|---|
| | 0.8 | 1 | 2 | 3 | 4 | 5 |
| TrxHa1-210 | 0.00 | 7.46 | 1.02 | 0.6 | 11.36 | 3.04 |
| Standard Deviation | 0.00 | 1.86 | 0.92 | 2.62 | 1.81 | 4.78 |
| TrxHa1-210DD | 0.00 | 6.88 | 3.55 | 8.75 | 18.75 | 21.45 |
| Standard Deviation | 0.00 | 3.24 | 2.12 | 5.88 | 4.13 | 4.76 |

As confirmed in the above results, the oral administration of hAChR α subunit polypeptide lacking B cell epitope to an animal model with myasthenia gravis slows down the weight loss, which is a typical symptom carried by the administration of hAChR α subunit polypeptide (FIG. 6).

TABLE 2

Clinical score determined after the oral administration of hAChR α subunit lacking B cell epitope

| | Week | | | | | |
|---|---|---|---|---|---|---|
| | 0.8 | 1 | 2 | 3 | 4 | 5 |
| TrxHa1-210 | 0.00 | 0.50 | 0.90 | 0.90 | 0.70 | 2.20 |
| Standard Deviation | 0.00 | 0.22 | 0.19 | 0.29 | 0.12 | 0.49 |
| TrxHa1-210DD | 0.5 | 1 | 0.625 | 0.875 | 0.25 | 0.5 |
| Standard Deviation | 0.50 | 0.58 | 0.13 | 0.38 | 0.14 | 0.35 |

As confirmed in the above results, the oral administration of hAChR α subunit polypeptide lacking B cell epitope to an animal model with myasthenia gravis resulted in not worse clinical score than that resulted from the oral administration of hAChR α subunit polypeptide (FIG. 7).

Example 4

Preparation of a Polypeptide Composed of CD4 T Cell Epitopes of hAChR α, β, γ and ε Chains Reacting to Myasthenia Gravis Patient Nucleotide sequence composing the active site reacting to CD4+ T cells was designed to be composed of two major parts; which are part A comprising 13 oligomers represented by SEQ. ID. NO: 7-NO: 19 and part B comprising 12 oligomers represented by SEQ. ID. NO: 20-NO: 31 (FIG. 8). To obtain a DNA to which CD4+ T cell active sites are serially linked, 13 and 12 single-stranded DNA oligomers, respectively for part A and part B, were ordered at Cosmogenetech (Korea). 25 pmol of each oligomer was mixed with 2.5 unit of Pfu, 4 µl of dNTP and 45 µl of distilled water, followed by PCR at 94° C. for 30 seconds, at 52° C. for 30 seconds and at 72° C. for 120 seconds (24 cycles). 1 µl of the final reaction solution was reacted with 1 unit of ligase of pGEM-easy cloning kit (Promega, USA) and ligase buffer for 12 hours at 16° C. to produce plasmid pGEM-PartA and pGEM-PartB. 50 µg of these vectors were reacted with 10 unit of restriction enzyme Nco I at 37° C. for 6 hours to prepare DNA fragments, which were linked to pThio-HisA vector (Invitrogen, USA) using T4 ligase, resulting in the expression vector pThio-HisA-PartA-PartB (FIG. 9). Electrophoresis was performed to confirm the production of the plasmid vector (FIG. 10). The expression vector was used to prepare polypeptides in which CD4+ T cell active sites were fused by the same manner as described in Example 2 and the production of those polypeptides were confirmed by electrophoresis using 12% SDS-PAGE gel at 90 V for 2 hours (FIG. 11).

Example 5

Synthesis of Recombinant Polypeptides with T Cell Epitopes in hAChR (Hα1-210) are Fused 50 ng of pThio-HisA-PartA-PartB DNA prepared in Example 4 was reacted with 50 µl of E. coli Top 10 for 30 seconds at 42° C., which stood for 10 minutes thereafter. The reaction solution was placed in an ampicillin containing medium, followed by the selection of transformed E. coli cells. The selected E. coli cells were cultured in 5 ml LB medium for 10 hours at 37° C. and the culture solution was inoculated into 1 l LB medium, followed by further culture for 3 hours at 37° C. 1 mM of IPTG was added to the culture solution, followed by culture for four more hours. Centrifugation was performed with 10,000×g to separate E. coli cells from the culture solution. The isolated E. coli cells were washed twice with 50 mM Tris buffer and the cells were homogenized with a sonicator. The homogenized E. coli cells were diluted in 50 mM Tris buffer, followed by centrifugation at 10,000×g to remove the supernatant. Then, the precipitate was dissolved in 9 M urea solution, followed by centrifugation at 20,000×g for one hour. The supernatant was transferred onto the dialysis membrane, followed by dialysis with 50 mM Tris buffer 5 times every three hour. Centrifugation was performed at 20,000×g and as a result, a target polypeptide was obtained from the supernatant, which was named "TrxPartA-PartB". The polypeptide was electrophoresed on 12% SDS PAGE gel with 90 V for 2 hours and then transferred onto a nitrocellulose membrane (Biored, USA), followed by Western blotting. After the transfer, the nitrocellulose membrane was reacted in a PBS solution containing 5% skim milk at room temperature for one hour to block the polypeptide-not-transferred regions. Western blotting was performed by using a monoclonal antibody (mAb 198, produced by Dr. Socrates Tzartos, Greece) having an affinity for MIR (main immunogenic region) of hAChR. Particularly, the membrane was reacted in PBS buffer containing the monoclonal antibody mAb198 for 90 minutes and then washed three times with PBS. The membrane was reacted again in PBS containing anti-mouse IgG-HRP (Sigma, USA) for 60 minutes and then washed three times with PBS. The membrane was then reacted with ECL kit (Amersham Biosciences, UK) for one minute and then exposed on X-ray film.

Example 6-Example 10

Investigation on Weight Changes and Clinical Scoring after Oral Administration of Recombinant Polypeptides Composed of all CD4 T Cell Epitopes of hAChR Recombinant polypeptides with various combinations of T cell epitopes were prepared in Example 6-Example 10 by the same manner as described in Example 4 and Example 5. The combinations of T cell epitopes are shown in Table 3.

TABLE 3

Polypeptides with the combinations of T cell epitopes

| Name | Combination |
| --- | --- |
| Example 4 | β 181–200, β 271–290, β 316–350, γ 75–94, γ 321–340, ε 91–110, ε 141–160 |
| Example 6 | α 48–67, α 101–120, α 118–167, α 304–328, α 403–421, α 419–437, β 181–200, β 271–290, β 316–350, γ 75–94, γ 321–340, ε 91–110, ε 141–160 |
| Example 7 | β 181–200, β 271–290, β 316–350, γ 75–94, γ 321–340 |
| Example 8 | β 181–200, β 271–290, β 316–350, ε 91–110, ε 141–160 |
| Example 9 | α 48–67, α 101–120, α 118–167, α 304–328, α 403–421, α 419–437, β 181–200, β 271–290, β 316-350, γ 75–94, γ 321–340 |
| Example 10 | α 48–67, α 101–120, α 118–167, α 304–328, α 403–421, α 419–437, β 181–200, β 271–290, β 316–350, ε 91–110, ε 141–160 |

Weight changes were observed in mice administered orally with recombinant polypeptides with the combinations of T cell epitopes prepared as shown in Table 3 by the same manner as described in Example 3, followed by clinical scoring. The results are shown in Table 4 and Table 5.

TABLE 4

Weight changes after oral administration of recombinant polypeptides with the combinations of T cell epitopes

| | Week | | | | | |
| --- | --- | --- | --- | --- | --- | --- |
| | 0.8 | 1 | 2 | 3 | 4 | 5 |
| ThrHa1-210 | 0.00 | 7.46 | 1.02 | 0.6 | 11.36 | 3.04 |
| Standard Deviation | 0.00 | 8.05 | 9.61 | 12.92 | 15.74 | 21.51 |
| Example 4 | 0.00 | 4.01 | 3.10 | 4.45 | 6.23 | 9.36 |
| Standard Deviation | 0.00 | 2.24 | 5.30 | 4.21 | 3.24 | 8.22 |
| Example 6 | 0.00 | 1.86 | 0.92 | 2.62 | 1.81 | 4.78 |
| Standard Deviation | 0.00 | 6.5 | 8.3 | 10.2 | 13.9 | 19.2 |
| Example 7 | 0.00 | 6.24 | 8.90 | 11.01 | 12.36 | 17.58 |
| Standard Deviation | 0.00 | 1.35 | 2.00 | 5.21 | 3.39 | 5.70 |
| Example 8 | 0.00 | 8.57 | 10.90 | 9.84 | 11.85 | 15.21 |
| Standard Deviation | 0.00 | 3.89 | 4.05 | 3.00 | 2.29 | 5.98 |
| Example 9 | 0.00 | 5.52 | 7.76 | 9.36 | 14.55 | 20.34 |
| Standard Deviation | 0.00 | 0.05 | 1.17 | 4.50 | 3.78 | 9.10 |
| Example 10 | 0.00 | 9.95 | 13.78 | 16.88 | 18.21 | 20.11 |
| Standard Deviation | 0.00 | 4.64 | 7.10 | 4.64 | 3.96 | 5.99 |

As confirmed from the above results, weight loss was alleviated in an animal model with myasthenia gravis by the oral administration of polypeptides with the combinations of T cell epitopes.

TABLE 5

Clinical scores according after oral administration of recombinant polypeptides with the combinations of T cell epitopes

| | Week | | | | | |
| --- | --- | --- | --- | --- | --- | --- |
| | 0.8 | 1 | 2 | 3 | 4 | 5 |
| TrxHa1-210 | 0.00 | 0.50 | 0.90 | 0.90 | 0.70 | 2.20 |
| Standard Deviation | 0.00 | 0.22 | 0.19 | 0.29 | 0.12 | 0.49 |
| Example 4 | 0.5 | 1 | 0.87 | 0.64 | 0.25 | 0.31 |
| Standard Deviation | 0.4 | 0.51 | 0.51 | 0.27 | 0.19 | 0.15 |
| Example 6 | 0.65 | 0.98 | 0.71 | 0.47 | 0.29 | 0.30 |
| Standard Deviation | 0.10 | 0.21 | 0.19 | 0.26 | 0.14 | 0.12 |
| Example 7 | 0.45 | 1 | 0.85 | 0.63 | 0.41 | 0.32 |
| Standard Deviation | 0.21 | 0.51 | 0.54 | 0.31 | 0.19 | 0.10 |
| Example 8 | 0.30 | 1.2 | 0.95 | 0.69 | 0.48 | 0.62 |
| Standard Deviation | 0.10 | 0.30 | 0.19 | 0.47 | 0.29 | 0.17 |
| Example 9 | 0.35 | 1 | 0.71 | 0.52 | 0.33 | 0.30 |
| Standard Deviation | 0.29 | 0.54 | 0.33 | 0.24 | 0.11 | 0.19 |
| Example 10 | 0.87 | 0.99 | 0.62 | 0.44 | 0.39 | 0.32 |
| Standard Deviation | 0.41 | 0.12 | 0.26 | 0.21 | 0.17 | 0.15 |

As shown in the above results, the worsening of the clinical score was relieved by the oral administration of recombinant polypeptides with the combinations of T cell epitopes to an animal model with myasthenia gravis.

INDUSTRIAL APPLICABILITY

As explained hereinbefore, polypeptides with the deletion of B cell epitope of hAChR α subunit or with the recombinant chimeric AChR composed of CD4 T cell epitopes relieve the symptoms of myasthenia gravis in animal models. Therefore, the composition containing the polypeptide above or two or more the polypeptides above can be effectively used as a therapeutic agent specifically working on myasthenia gravis and/or immunomodulator without side-effects.

What is claimed is:

1. A recombinant muscle acetylcholine receptor α subunit polypeptide with a deletion of one or more B cell epitopes, wherein the polypeptide is prepared by deleting one or more B cell epitopes from a full length muscle acetylcholine receptor α subunit having an amino acid sequence of SEQ ID NO:56 and the B cell epitope has an amino acid sequence comprising amino acids 67 to 76 and/or 129 to 145 of SEQ ID NO:56.

2. A therapeutic agent for myasthenia gravis containing the polypeptide of claim 1 as an effective ingredient.

* * * * *

```
                        SEQUENCE LISTING

<160> NUMBER OF SEQ ID NOS: 61

<210> SEQ ID NO 1
<211> LENGTH: 24
<212> TYPE: DNA
<213> ORGANISM: Artificial Sequence
<220> FEATURE:
<223> OTHER INFORMATION: hAChR sense primer

<400> SEQUENCE: 1
```

```
ccggtacctt ccgaacatga gacc                                          24

<210> SEQ ID NO 2
<211> LENGTH: 22
<212> TYPE: DNA
<213> ORGANISM: Artificial Sequence
<220> FEATURE:
<223> OTHER INFORMATION: hAChR antisense primer

<400> SEQUENCE: 2
cggaattcca ggcgctgcat ga                                            22

<210> SEQ ID NO 3
<211> LENGTH: 49
<212> TYPE: DNA
<213> ORGANISM: Artificial Sequence
<220> FEATURE:
<223> OTHER INFORMATION: deletion sense primer 1

<400> SEQUENCE: 3
caatgggtgg attacaacct aaaaaaaatt cacattcctt cagaaaaga               49

<210> SEQ ID NO 4
<211> LENGTH: 50
<212> TYPE: DNA
<213> ORGANISM: Artificial Sequence
<220> FEATURE:
<223> OTHER INFORMATION: deletion antisense primer 1

<400> SEQUENCE: 4
atcttttctg aaggaatgtg aattttttt aggttgtaat ccacccattg                50

<210> SEQ ID NO 5
<211> LENGTH: 34
<212> TYPE: DNA
<213> ORGANISM: Artificial Sequence
<220> FEATURE:
<223> OTHER INFORMATION: deletion sense primer 2

<400> SEQUENCE: 5
catctttaaa agctactgtc tgggcacctg gacc                               34

<210> SEQ ID NO 6
<211> LENGTH: 33
<212> TYPE: DNA
<213> ORGANISM: Artificial Sequence
<220> FEATURE:
<223> OTHER INFORMATION: deletion antisense primer 2

<400> SEQUENCE: 6
ggtccaggtg gccagacagt agcttttaaa gat                                33

<210> SEQ ID NO 7
<211> LENGTH: 22
<212> TYPE: DNA
<213> ORGANISM: Artificial Sequence
<220> FEATURE:
<223> OTHER INFORMATION: Part A oligomer 1

<400> SEQUENCE: 7
gctctagaag agaatggcca gt                                            22

<210> SEQ ID NO 8
<211> LENGTH: 47
<212> TYPE: DNA
```

```
<213> ORGANISM: Artificial Sequence
<220> FEATURE:
<223> OTHER INFORMATION: Part A oligomer 2

<400> SEQUENCE: 8
ggagaatatc cacaagccct ctcggctaat ccagcctcca ggcgatc          47

<210> SEQ ID NO 9
<211> LENGTH: 50
<212> TYPE: DNA
<213> ORGANISM: Artificial Sequence
<220> FEATURE:
<223> OTHER INFORMATION: Part A oligomer 3

<400> SEQUENCE: 9
tggctgacaa agtacctgag acctcactat cagtacccat tattatcaag       50

<210> SEQ ID NO 10
<211> LENGTH: 45
<212> TYPE: DNA
<213> ORGANISM: Artificial Sequence
<220> FEATURE:
<223> OTHER INFORMATION: Part A oligomer 4

<400> SEQUENCE: 10
tacctcatga cccaccaaat gcccctttgg gtccgtcaga tcttc            45

<210> SEQ ID NO 11
<211> LENGTH: 47
<212> TYPE: DNA
<213> ORGANISM: Artificial Sequence
<220> FEATURE:
<223> OTHER INFORMATION: Part A oligomer 5

<400> SEQUENCE: 11
ttcacaaact tccgctgtac ctgcgtctaa aaaggcccaa acccgag          47

<210> SEQ ID NO 12
<211> LENGTH: 42
<212> TYPE: DNA
<213> ORGANISM: Artificial Sequence
<220> FEATURE:
<223> OTHER INFORMATION: Part A oligomer 6

<400> SEQUENCE: 12
agagacctga tgccggagcc cctgtgggtg ctgagggtgc cg               42

<210> SEQ ID NO 13
<211> LENGTH: 21
<212> TYPE: DNA
<213> ORGANISM: Artificial Sequence
<220> FEATURE:
<223> OTHER INFORMATION: Part A oligomer 7

<400> SEQUENCE: 13
tccaccatgg tgtggcggcc g                                      21

<210> SEQ ID NO 14
<211> LENGTH: 47
<212> TYPE: DNA
<213> ORGANISM: Artificial Sequence
<220> FEATURE:
<223> OTHER INFORMATION: Part A oligomer 8

<400> SEQUENCE: 14
cgagatcttc tcttaccggt caccctctta taggtgttcg ggagagc          47
```

<210> SEQ ID NO 15
<211> LENGTH: 44
<212> TYPE: DNA
<213> ORGANISM: Artificial Sequence
<220> FEATURE:
<223> OTHER INFORMATION: Part A oligomer 9

<400> SEQUENCE: 15
gattaggtcg gaggtccgct agaccgactg tttcatggac tctg                             44

<210> SEQ ID NO 16
<211> LENGTH: 50
<212> TYPE: DNA
<213> ORGANISM: Artificial Sequence
<220> FEATURE:
<223> OTHER INFORMATION: Part A oligomer 10

<400> SEQUENCE: 16
agtgatagtc atgggtaata atagttcatg gagtactggg tggtttacgg                       50

<210> SEQ ID NO 17
<211> LENGTH: 46
<212> TYPE: DNA
<213> ORGANISM: Artificial Sequence
<220> FEATURE:
<223> OTHER INFORMATION: Part A oligomer 11

<400> SEQUENCE: 17
ggaaacccag gcagtctaga agtaagtgtt tgaaggcgac atggac                           46

<210> SEQ ID NO 18
<211> LENGTH: 43
<212> TYPE: DNA
<213> ORGANISM: Artificial Sequence
<220> FEATURE:
<223> OTHER INFORMATION: Part A oligomer 12

<400> SEQUENCE: 18
cagatttttc cgggtttggg ctctctctgg actacggcct cgg                              43

<210> SEQ ID NO 19
<211> LENGTH: 42
<212> TYPE: DNA
<213> ORGANISM: Artificial Sequence
<220> FEATURE:
<223> OTHER INFORMATION: Part A oligomer 13

<400> SEQUENCE: 19
gacacccacg actcccacgg caggcggtac cacaccgccg gc                               42

<210> SEQ ID NO 20
<211> LENGTH: 42
<212> TYPE: DNA
<213> ORGANISM: Artificial Sequence
<220> FEATURE:
<223> OTHER INFORMATION: Part B oligomer 1

<400> SEQUENCE: 20
tccaccatgg tgtggcggcc ggatatcgtg ctggaggggg tc                               42

<210> SEQ ID NO 21
<211> LENGTH: 43
<212> TYPE: DNA
<213> ORGANISM: Artificial Sequence
<220> FEATURE:

<223> OTHER INFORMATION: Part B oligomer 2

<400> SEQUENCE: 21
gcaaggtgtt cctgaggctc ttgccccagc tgctgaggat gca				43

<210> SEQ ID NO 22
<211> LENGTH: 46
<212> TYPE: DNA
<213> ORGANISM: Artificial Sequence
<220> FEATURE:
<223> OTHER INFORMATION: Part B oligomer 3

<400> SEQUENCE: 22
gttcgcccgc tggccgtgct ggaaaacaat attgatggcc agttcg				46

<210> SEQ ID NO 23
<211> LENGTH: 45
<212> TYPE: DNA
<213> ORGANISM: Artificial Sequence
<220> FEATURE:
<223> OTHER INFORMATION: Part B oligomer 4

<400> SEQUENCE: 23
gagtggccta cgacgccaac gtgctcgtca actgttcgct tattt				45

<210> SEQ ID NO 24
<211> LENGTH: 46
<212> TYPE: DNA
<213> ORGANISM: Artificial Sequence
<220> FEATURE:
<223> OTHER INFORMATION: Part B oligomer 5

<400> SEQUENCE: 24
ccgctctcag acgtacaatg ccgaagaggt ggagttcact tttacc				46

<210> SEQ ID NO 25
<211> LENGTH: 20
<212> TYPE: DNA
<213> ORGANISM: Artificial Sequence
<220> FEATURE:
<223> OTHER INFORMATION: Part B oligomer 6

<400> SEQUENCE: 25
gcagcgctgc tgaggatgca				20

<210> SEQ ID NO 26
<211> LENGTH: 20
<212> TYPE: DNA
<213> ORGANISM: Artificial Sequence
<220> FEATURE:
<223> OTHER INFORMATION: Part B oligomer 7

<400> SEQUENCE: 26
aggtggtacc acaccgccgg				20

<210> SEQ ID NO 27
<211> LENGTH: 44
<212> TYPE: DNA
<213> ORGANISM: Artificial Sequence
<220> FEATURE:
<223> OTHER INFORMATION: Part B oligomer 8

<400> SEQUENCE: 27
ctatagcacg acctccccca ggcgttccac aaggactccg agaa				44

<210> SEQ ID NO 28
<211> LENGTH: 42
<212> TYPE: DNA
<213> ORGANISM: Artificial Sequence
<220> FEATURE:
<223> OTHER INFORMATION: Part B oligomer 9

<400> SEQUENCE: 28
ggggtcgacg actcctacgt gcaagcgggc gaccggcacg ac                           42

<210> SEQ ID NO 29
<211> LENGTH: 46
<212> TYPE: DNA
<213> ORGANISM: Artificial Sequence
<220> FEATURE:
<223> OTHER INFORMATION: Part B oligomer 10

<400> SEQUENCE: 29
cttttgttat aactaccggt caagcctcac cggatgctgc ggttgc                       46

<210> SEQ ID NO 30
<211> LENGTH: 46
<212> TYPE: DNA
<213> ORGANISM: Artificial Sequence
<220> FEATURE:
<223> OTHER INFORMATION: Part B oligomer 11

<400> SEQUENCE: 30
acgagcagtt gacaagcgaa taaaaggcga gagtctgcat gttacg                       46

<210> SEQ ID NO 31
<211> LENGTH: 45
<212> TYPE: DNA
<213> ORGANISM: Artificial Sequence
<220> FEATURE:
<223> OTHER INFORMATION: Part B oligomer 12

<400> SEQUENCE: 31
cttctccacc tcaagtgaaa atggacgtcg cgacgactcc tacgt                        45

<210> SEQ ID NO 32
<211> LENGTH: 224
<212> TYPE: PRT
<213> ORGANISM: Artificial Sequence
<220> FEATURE:
<223> OTHER INFORMATION: B cell epitope 67-76 deletion peptide

<400> SEQUENCE: 32

Ser Glu His Glu Thr Arg Leu Val Ala L

```
                    115                 120                 125
Gly His Ile Thr Trp Thr Pro Pro Ala Ile Phe Lys Ser Tyr Cys Glu
    130                 135                 140

Ile Ile Val Thr His Phe Pro Phe Asp Glu Gln Asn Cys Ser Met Lys
145                 150                 155                 160

Leu Gly Thr Trp Thr Tyr Asp Gly Ser Val Val Ala Ile Asn Pro Glu
                165                 170                 175

Ser Asp Gln Pro Asp Leu Ser Asn Phe Met Glu Ser Gly Gln Trp Val
            180                 185                 190

Ile Lys Glu Ser Arg Gly Trp Lys His Ser Val Thr Tyr Ser Cys Cys
        195                 200                 205

Pro Asp Thr Pro Tyr Leu Asp Ile Thr Tyr His Phe Val Met Gln Arg
    210                 215                 220
```

<210> SEQ ID NO 33
<211> LENGTH: 218
<212> TYPE: PRT
<213> ORGANISM: Artificial Sequence
<220> FEATURE:
<223> OTHER INFORMATION: B cell epitope 129-145 deletion peptide

<400> SEQUENCE: 33

```
Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile

-continued

<400> SEQUENCE: 34

```
Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25                  30

Val Gly Leu Gln Leu Ile Gln Leu Ile Asn Val Asp Glu Val Asn Gln
        35                  40                  45

Ile Val Thr Thr Asn Val Arg Leu Lys Gln Gly Asp Met Val Asp Leu
    50                  55                  60

Pro Arg Pro Ser Cys Val Thr Leu Gly Val Pro Leu Phe Ser His Leu
65                  70                  75                  80

Gln Asp Glu Gln Trp Val Asp Tyr Asn Leu Lys Lys Ile His Ile Pro
                85                  90                  95

Ser Glu Lys Ile Trp Arg Pro Asp Leu Val Leu Tyr Asn Asp Ala Asp
            100                 105                 110

Gly Asp Phe Ala Ile Val Lys Phe Thr Lys Val Leu Leu Gln Tyr Thr
        115                 120                 125

Gly His Ile Thr Trp Thr Pro Pro Ala Ile Phe Lys Ser Tyr Cys Leu
    130                 135                 140

Gly Thr Trp Thr Tyr Asp Gly Ser Val Val Ala Ile Asn Pro Glu Ser
145                 150                 155                 160

Asp Gln Pro Asp Leu Ser Asn Phe Met Glu Ser Gly Gln Trp Val Ile
                165                 170                 175

Lys Glu Ser Arg Gly Trp Lys His Ser Val Thr Tyr Ser Cys Cys Pro
            180                 185                 190

Asp Thr Pro Tyr Leu Asp Ile Thr Tyr His Phe Val Met Gln Arg Leu
        195                 200                 205
```

<210> SEQ ID NO 35
<211> LENGTH: 681
<212> TYPE: DNA
<213> ORGANISM: Artificial Sequence
<220> FEATURE:
<223> OTHER INFORMATION: DNA sequence of B cell epitope 67-76 deletion peptide

<400> SEQUENCE: 35

```
tccgaacatg agacccgtct ggtggcaaag ctatttaaag actacagcag cgtggtgcgg     60
ccagtggaag accaccgcca ggtcgtggag gtcaccgtgg gcctgcagct gatacagctc    120
atcaatgtgg atgaagtaaa tcagatcgtg acaaccaatg tgcgtctgaa acagggtgac    180
atggtagatc tgccacgccc cagctgcgtg actttgggag ttcctttgtt ttctcatctg    240
caggatgagc aatgggtgga ttacaaccta aaaaaaattc acattccttc agaaaagatc    300
tggcgcccag accttgttct ctataacgat gcagatggtg actttgctat tgtcaagttc    360
accaaagtgc tcctgcagta cactggccac atcacgtgga cacctccagc catctttaaa    420
agctactgtg agatcatcgt cacccacttt ccctttgatg aacagaactg cagcatgaag    480
ctgggcacct ggacctacga cggctctgtc gtggccatca acccggaaag cgaccagcca    540
gacctgagca acttcatgga gagcgggcag tgggtgatca aggagtcccg gggctggaag    600
cactccgtga cctattcctg ctgccccgac accccctacc tggacatcac ctaccacttc    660
gtcatgcagc gcctgtgata g                                              681
```

<210> SEQ ID NO 36

-continued

<211> LENGTH: 660
<212> TYPE: DNA
<213> ORGANISM: Artificial Sequence
<220> FEATURE:
<223> OTHER INFORMATION: DNA sequence of B cell epitope 129-145 deletion peptide

<400> SEQUENCE: 36

```
tccgaacatg agacccgtct ggtggcaaag ctatttaaag actacagcag cgtggtgcgg     60
ccagtggaag accaccgcca ggtcgtggag gtcaccgtgg gcctgcagct gatacagctc    120
atcaatgtgg atgaagtaaa tcagatcgtg acaaccaatg tgcgtctgaa acagggtgac    180
atggtagatc tgccacgccc cagctgcgtg actttgggag ttcctttgtt ttctcatctg    240
caggatgagc aatgggtgga ttacaaccta aaatggaatc cagatgacta tggcggtgtg    300
aaaaaaattc acattccttc agaaaagatc tggcgcccag accttgttct ctataacgat    360
gcagatggtg actttgctat tgtcaagttc accaaagtgc tcctgcagta cactggccac    420
atcacgtgga cacctccagc catctttaaa agctactgtc tgggcacctg gacctacgac    480
ggctctgtcg tggccatcaa cccggaaagc gaccagccag acctgagcaa cttcatggag    540
agcgggcagt gggtgatcaa ggagtcccgg ggctggaagc actccgtgac ctattcctgc    600
tgccccgaca ccccctacct ggacatcacc taccacttcg tcatgcagcg cctgtgatag    660
```

<210> SEQ ID NO 37
<211> LENGTH: 630
<212> TYPE: DNA
<213> ORGANISM: Artificial Sequence
<220> FEATURE:
<223> OTHER INFORMATION: DNA sequcence of B cell epitope 67-76,129-145 deletion peptide

<400> SEQUENCE: 37

```
tccgaacatg agacccgtct ggtggcaaag ctatttaaag actacagcag cgtggtgcgg     60
ccagtggaag accaccgcca ggtcgtggag gtcaccgtgg gcctgcagct gatacagctc    120
atcaatgtgg atgaagtaaa tcagatcgtg acaaccaatg tgcgtctgaa acagggtgac    180
atggtagatc tgccacgccc cagctgcgtg actttgggag ttcctttgtt ttctcatctg    240
caggatgagc aatgggtgga ttacaaccta aaaaaaattc acattccttc agaaaagatc    300
tggcgcccag accttgttct ctataacgat gcagatggtg actttgctat tgtcaagttc    360
accaaagtgc tcctgcagta cactggccac atcacgtgga cacctccagc catctttaaa    420
agctactgtc tgggcacctg gacctacgac ggctctgtcg tggccatcaa cccggaaagc    480
gaccagccag acctgagcaa cttcatggag agcgggcagt gggtgatcaa ggagtcccgg    540
ggctggaagc actccgtgac ctattcctgc tgccccgaca ccccctacct ggacatcacc    600
taccacttcg tcatgcagcg cctgtgatag                                    630
```

<210> SEQ ID NO 38
<211> LENGTH: 20
<212> TYPE: PRT
<213> ORGANISM: Artificial Sequence
<220> FEATURE:
<223> OTHER INFORMATION: T cell epitope alpha 48-67

<400> SEQUENCE: 38

```
Gln Ile Val Thr Thr Asn Val Arg Leu Lys Gln Gln Trp Val Asp Tyr
1               5                   10                  15

Asn Leu Lys Trp
            20
```

```
<210> SEQ ID NO 39
<211> LENGTH: 20
<212> TYPE: PRT
<213> ORGANISM: Artificial Sequence
<220> FEATURE:
<223> OTHER INFORMATION: T cell epitope alpha 101-120

<400> SEQUENCE: 39

Ala Ile Val Lys Phe Thr Lys Val Leu Leu Gln Tyr Thr Gly His Ile
1               5                   10                  15
Thr Trp Thr Pro
            20

<210> SEQ ID NO 40
<211> LENGTH: 20
<212> TYPE: PRT
<213> ORGANISM: Artificial Sequence
<220> FEATURE:
<223> OTHER INFORMATION: T cell epitope alpha 118-137

<400> SEQUENCE: 40

Trp Thr Pro Pro Ala Ile Phe Lys Ser Tyr Cys Glu Ile Ile Val Thr
1               5                   10                  15
His Phe Pro Phe
            20

<210> SEQ ID NO 41
<211> LENGTH: 22
<212> TYPE: PRT
<213> ORGANISM: Artificial Sequence
<220> FEATURE:
<223> OTHER INFORMATION: T cell epitope alpha 304-328

<400> SEQUENCE: 41

Ser Thr His Val Met Pro Asn Trp Val Arg Lys Val Phe Ile Asp Thr
1               5                   10                  15
Ile Pro Asn Ile Met Phe
            20

<210> SEQ ID NO 42
<211> LENGTH: 18
<212> TYPE: PRT
<213> ORGANISM: Artificial Sequence
<220> FEATURE:
<223> OTHER INFORMATION: T cell eiptope alpha 403-421

<400> SEQUENCE: 42

Ala Met Val Met Asp His Ile Leu Leu Gly Val Met Leu Val Cys Ile
1               5                   10                  15
Ile Gly

<210> SEQ ID NO 43
<211> LENGTH: 19
<212> TYPE: PRT
<213> ORGANISM: Artificial Sequence
<220> FEATURE:
<223> OTHER INFORMATION: T cell epitope alpha 419-437

<400> SEQUENCE: 43

Ile Ile Gly Thr Leu Ala Val Phe Ala Gly Arg Leu Ile Glu Leu Asn
1               5                   10                  15
Gln Gln Gly
```

```
<210> SEQ ID NO 44
<211> LENGTH: 20
<212> TYPE: PRT
<213> ORGANISM: Artificial Sequence
<220> FEATURE:
<223> OTHER INFORMATION: T cell epitope beta 181-210 peptide

<400> SEQUENCE: 44

Glu Asn Gly Gln Trp Glu Asn Ile His Lys Pro Ser Arg Leu Ile Gln
1               5                   10                  15

Pro Pro Gly Asp
            20

<210> SEQ ID NO 45
<211> LENGTH: 20
<212> TYPE: PRT
<213> ORGANISM: Artificial Sequence
<220> FEATURE:
<223> OTHER INFORMATION: T cell epitope beta 271-290 peptide

<400> SEQUENCE: 45

Leu Ala Asp Lys Val Pro Glu Thr Ser Leu Ser Val Pro Ile Ile Ile
1               5                   10                  15

Lys Tyr Leu Met
            20

<210> SEQ ID NO 46
<211> LENGTH: 35
<212> TYPE: PRT
<213> ORGANISM: Artificial Sequence
<220> FEATURE:
<223> OTHER INFORMATION: T cell epitope beta 316-350 peptide

<400> SEQUENCE: 46

Thr His Gln Met Pro Leu Trp Val Arg Gln Ile Phe Ile His Lys Leu
1               5                   10                  15

Pro Leu Tyr Leu Arg Leu Lys Arg Pro Lys Pro Glu Arg Asp Leu Met
            20                  25                  30

Pro Glu Pro
        35

<210> SEQ ID NO 47
<211> LENGTH: 20
<212> TYPE: PRT
<213> ORGANISM: Artificial Sequence
<220> FEATURE:
<223> OTHER INFORMATION: T cell epitope gamma 75-94 peptide

<400> SEQUENCE: 47

Leu Trp Val Leu Arg Val Pro Ser Thr Met Val Trp Arg Pro Asp Ile
1               5                   10                  15

Val Leu Glu Asn
            20

<210> SEQ ID NO 48
<211> LENGTH: 21
<212> TYPE: PRT
<213> ORGANISM: Artificial Sequence
<220> FEATURE:
<223> OTHER INFORMATION: T cell epitope gamma 321-340 peptide

<400> SEQUENCE: 48

Gly Val Arg Lys Val Phe Leu Arg Leu Leu Pro Gln Leu Leu Arg Met
1               5                   10                  15
```

```
His Val Arg Pro Leu
            20

<210> SEQ ID NO 49
<211> LENGTH: 20
<212> TYPE: PRT
<213> ORGANISM: Artificial Sequence
<220> FEATURE:
<223> OTHER INFORMATION: T cell epitope upsilon 91-110 peptide

<400> SEQUENCE: 49

Ala Val Leu Glu Asn Asn Ile Asp Gly Gln Phe Gly Val Ala Tyr Asp
1               5                   10                  15

Ala Asn Val Leu
            20

<210> SEQ ID NO 50
<211> LENGTH: 20
<212> TYPE: PRT
<213> ORGANISM: Artificial Sequence
<220> FEATURE:
<223> OTHER INFORMATION: T cell epitope upsilon 141-160 peptide

<400> SEQUENCE: 50

Val Asn Cys Ser Leu Ile Phe Arg Ser Gln Thr Tyr Asn Ala Glu Glu
1               5                   10                  15

Val Glu Phe Thr
            20

<210> SEQ ID NO 51
<211> LENGTH: 156
<212> TYPE: PRT
<213> ORGANISM: Artificial Sequence
<220> FEATURE:
<223> OTHER INFORMATION: T cell epitope combination peptide
      (beta,gamma,upsilon)

<400> SEQUENCE: 51

Glu Asn Gly Gln Trp Glu Asn Ile His Lys Pro Ser Arg Leu Ile Gln
1               5                   10                  15

Pro Pro Gly Asp Leu Ala Asp Lys Val Pro Glu Thr Ser Leu Ser Val
                20                  25                  30

Pro Ile Ile Ile Lys Tyr Leu Met Thr His Gln Met Pro Leu Trp Val
            35                  40                  45

Arg Gln Ile Phe Ile His Lys Leu Pro Leu Tyr Leu Arg Leu Lys Arg
        50                  55                  60

Pro Lys Pro Glu Arg Asp Leu Met Pro Glu Pro Leu Trp Val Leu Arg
65                  70                  75                  80

Val Pro Ser Thr Met Val Trp Arg Pro Asp Ile Val Leu Glu Gly Val
                85                  90                  95

Arg Lys Val Phe Leu Arg Leu Leu Pro Gln Leu Leu Arg Met His Val
            100                 105                 110

Arg Pro Leu Ala Val Leu Glu Asn Asn Ile Asp Gly Gln Phe Gly Val
        115                 120                 125

Ala Tyr Asp Ala Asn Val Leu Val Asn Cys Ser Leu Ile Phe Arg Ser
    130                 135                 140

Gln Thr Tyr Asn Ala Glu Glu Val Glu Phe Thr Phe
145                 150                 155

<210> SEQ ID NO 52
```

-continued

<211> LENGTH: 468
<212> TYPE: DNA
<213> ORGANISM: Artificial Sequence
<220> FEATURE:
<223> OTHER INFORMATION: DNA sequence of T cell epitope combination
peptide(beta,gamma,upsilon)

<400> SEQUENCE: 52

```
gagaatggcc agtgggagaa tatccacaag ccctctcggc taatccagcc tccaggcgat     60
ctggctgaca aagtacctga gacctcacta tcagtaccca ttattatcaa gtacctcatg    120
acccaccaaa tgcccctttg ggtccgtcag atcttcattc acaaacttcc gctgtacctg    180
cgtctaaaaa ggcccaaacc cgagagagac ctgatgccgg agcccctgtg ggtgctgagg    240
gtgccgtcca ccatggtgtg gcggccggat atcgtgctgg agggggtccg caaggtgttc    300
ctgaggctct tgccccagct gctgaggatg cacgttcgcc cgctggccgt gctggaaaac    360
aatattgatg gccagttcgg agtggcctac gacgccaacg tgctcgtcaa ctgttcgctt    420
attttccgct ctcagacgta caatgccgaa gaggtggagt tcactttt                 468
```

<210> SEQ ID NO 53
<211> LENGTH: 275
<212> TYPE: PRT
<213> ORGANISM: Artificial Sequence
<220> FEATURE:
<223> OTHER INFORMATION: Total T cell epitope combination
peptide(alpha,beta,gamma,upsilon)

<400> SEQUENCE: 53

```
Gln Ile Val Thr Thr Asn Val Arg Leu Lys Gln Gln Trp Val Asp Tyr
1               5                   10                  15

Asn Leu Lys Trp Ala Ile Val Lys Phe Thr Lys Val Leu Leu Gln Tyr
            20                  25                  30

Thr Gly His Ile Thr Trp Thr Pro Trp Thr Pro Pro Ala Ile Phe Lys
        35                  40                  45

Ser Tyr Cys Glu Ile Ile Val Thr His Phe Pro Phe Ser Thr His Val
    50                  55                  60

Met Pro Asn Trp Val Arg Lys Val Phe Ile Asp Thr Ile Pro Asn Ile
65                  70                  75                  80

Met Phe Ala Met Val Met Asp His Ile Leu Leu Gly Val Met Leu Val
                85                  90                  95

Cys Ile Ile Gly Ile Ile Gly Thr Leu Ala Val Phe Ala Gly Arg Leu
            100                 105                 110

Ile Glu Leu Asn Gln Gln Gly Glu Asn Gly Gln Trp Glu Asn Ile His
        115                 120                 125

Lys Pro Ser Arg Leu Ile Gln Pro Pro Gly Asp Leu Ala Asp Lys Val
    130                 135                 140

Pro Glu Thr Ser Leu Ser Val Pro Ile Ile Ile Lys Tyr Leu Met Thr
145                 150                 155                 160

His Gln Met Pro Leu Trp Val Arg Gln Ile Phe Ile His Lys Leu Pro
                165                 170                 175

Leu Tyr Leu Arg Leu Lys Arg Pro Lys Pro Glu Arg Asp Leu Met Pro
            180                 185                 190

Glu Pro Leu Trp Val Leu Arg Val Pro Ser Thr Met Val Trp Arg Pro
        195                 200                 205

Asp Ile Val Leu Glu Gly Val Arg Lys Val Phe Leu Arg Leu Leu Pro
    210                 215                 220

Gln Leu Leu Arg Met His Val Arg Pro Leu Ala Val Leu Glu Asn Asn
```

-continued

```
             225                 230                 235                 240
Ile Asp Gly Gln Phe Gly Val Ala Tyr Asp Ala Asn Val Leu Val Asn
                245                 250                 255

Cys Ser Leu Ile Phe Arg Ser Gln Thr Tyr Asn Ala Glu Glu Val Glu
            260                 265                 270

Phe Thr Phe
        275
```

<210> SEQ ID NO 54
<211> LENGTH: 647
<212> TYPE: DNA
<213> ORGANISM: Artificial Sequence
<220> FEATURE:
<223> OTHER INFORMATION: DNA sequence of total T cell epitope
      combination peptide(alpha,bata,gamma,upsilon)

<400> SEQUENCE: 54

```
aaattgttac tactaatgtt cgtcttaaac aacaatgggt tgattataat cttaaatggg      60
ctattgttaa atttactaaa gttcttcttc aatatactgg tcatattact tggactcctt     120
ggactcctcc tgctattttt aaatcttatt gtgaaattat tgttactcat tttccttta     180
agaatggcca gtgggagaat atccacaagc cctctcggct aatccagcct ccaggcgatc     240
tggctgacaa gtacctgag acctcactat cagtacccat tattatcaag tacctcatga     300
cccaccaaat gccctttgg gtccgtcaga tcttcattca aaacttccg ctgtacctgc      360
gtctaaaaag gcccaaaccc gagagagacc tgatgccgga gcccctgtgg gtgctgaggg     420
tgccgtccac catggtgtgg cggccggata tcgtgctgga ggggtccgc aaggtgttcc      480
tgaggctctt gccccagctg ctgaggatgc acgttcgccc gctggccgtg ctggaaaaca     540
atattgatgg ccagttcgga gtggcctacg acgccaacgt gctcgtcaac tgttcgctta     600
ttttccgctc tcagacgtac aatgccgaag aggtggagtt cactttt                   647
```

<210> SEQ ID NO 55
<211> LENGTH: 364
<212> TYPE: PRT
<213> ORGANISM: Artificial Sequence
<220> FEATURE:
<223> OTHER INFORMATION: Total combination peptide(B cell epitope
      deletion, T cell epitope)

<400> SEQUENCE: 55

```
Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
            20                  25

```
Gly His Ile Thr Trp Thr Pro Pro Ala Ile Phe Lys Ser Tyr Cys Leu
    130                 135                 140

Gly Thr Trp Thr Tyr Asp Gly Ser Val Val Ala Ile Asn Pro Glu Ser
145                 150                 155                 160

Asp Gln Pro Asp Leu Ser Asn Phe Met Glu Ser Gly Gln Trp Val Ile
                165                 170                 175

Lys Glu Ser Arg Gly Trp Lys His Ser Val Thr Tyr Ser Cys Cys Pro
                180                 185                 190

Asp Thr Pro Tyr Leu Asp Ile Thr Tyr His Phe Val Met Gln Arg Leu
            195                 200                 205

Glu Asn Gly Gln Trp Glu Asn Ile His Lys Pro Ser Arg Leu Ile Gln
210                 215                 220

Pro Pro Gly Asp Leu Ala Asp Lys Val Pro Glu Thr Ser Leu Ser Val
225                 230                 235                 240

Pro Ile Ile Ile Lys Tyr Leu Met Thr His Gln Met Pro Leu Trp Val
                245                 250                 255

Arg Gln Ile Phe Ile His Lys Leu Pro Leu Tyr Leu Arg Leu Lys Arg
                260                 265                 270

Pro Lys Pro Glu Arg Asp Leu Met Pro Glu Pro Leu Trp Val Leu Arg
            275                 280                 285

Val Pro Ser Thr Met Val Trp Arg Pro Asp Ile Val Leu Glu Gly Val
290                 295                 300

Arg Lys Val Phe Leu Arg Leu Pro Gln Leu Leu Arg Met His Val
305                 310                 315                 320

Arg Pro Leu Ala Val Leu Glu Asn Asn Ile Asp Gly Gln Phe Gly Val
                325                 330                 335

Ala Tyr Asp Ala Asn Val Leu Val Asn Cys Ser Leu Ile Phe Arg Ser
            340                 345                 350

Gln Thr Tyr Asn Ala Glu Glu Val Glu Phe Thr Phe
        355                 360

<210> SEQ ID NO 56
<211> LENGTH: 210
<212> TYPE: PRT
<213> ORGANISM: Artificial Sequence
<220> FEATURE:
<223> OTHER INFORMATION: A recombinant polypeptide of acetylcholine
      receptor alpha subuint

<400> SEQUENCE: 56

Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
                20                  25                  30

Val Gly Leu Gln Leu Ile Gln Leu Ile Asn Val Asp Glu Val Asn Gln
            35                  40                  45

Ile Val Thr Thr Asn Val Arg Leu Lys Gln Gln Trp Val Asp Tyr Asn
        50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asp Ala
                85                  90                  95

Asp Gly Asp Phe Ala Ile Val Lys Phe Thr Lys Val Leu Leu Gln Tyr
            100                 105                 110

Thr Gly His Ile Thr Trp Thr Pro Pro Ala Ile Phe Lys Ser Tyr Cys
        115                 120                 125
```

```
Glu Ile Ile Val Thr His Phe Pro Phe Asp Glu Gln Asn Cys Ser Met
    130                 135                 140

Lys Leu Gly Thr Trp Thr Tyr Asp Gly Ser Val Val Ala Ile Asn Pro
145                 150                 155                 160

Glu Ser Asp Gln Pro Asp Leu Ser Asn Phe Met Glu Ser Gly Gln Trp
                165                 170                 175

Val Ile Lys Glu Ser Arg Gly Trp Lys His Ser Val Thr Tyr Ser Cys
            180                 185                 190

Cys Pro Asp Thr Pro Tyr Leu Asp Ile Thr Tyr His Phe Val Met Gln
        195                 200                 205

Arg Leu
    210

<210> SEQ ID NO 57
<211> LENGTH: 630
<212> TYPE: DNA
<213> ORGANISM: Artificial Sequence
<220> FEATURE:
<223> OTHER INFORMATION: DNA sequence of a recombinant polypeptide of
      acetylcholine receptor alpha subunit

<400> SEQUENCE: 57
tccgaacatg agaccgtct ggtggcaaag ctatttaaag actacagcag cgtggtgcgg     60
ccagtggaag accaccgcca ggtcgtggag gtcaccgtgg gcctgcagct gatacagctc    120
atcaatgtgg atgaagtaaa tcagatcgtg acaaccaatg tgcgtctgaa acagcaatgg    180
gtggattaca acctaaaatg gaatccagat gactatggcg gtgtgaaaaa aattcacatt    240
ccttcagaaa agatctggcg cccagacctt gttctctata cgatgcaga tggtgacttt    300 gctattgtca agttcaccaa agtgctcctg cagtacactg ccacatcac gtggacacct    360 ccagccatct ttaaaagcta ctgtgagatc atcgtcaccc actttccctt tgatgaacag    420
aactgcagca tgaagctggg cacctggacc tacgacggct ctgtcgtggc catcaacccg    480
gaaagcgacc agccagacct gagcaacttc atggagagcg gcagtgggt gatcaaggag    540 tcccggggct ggaagcactc cgtgacctat tcctgctgcc ccgacacccc ctacctggac    600
atcacctacc acttcgtcat gcagcgcctg                                    630

<210> SEQ ID NO 58
<211> LENGTH: 78
<212> TYPE: DNA
<213> ORGANISM: Artificial Sequence
<220> FEATURE:
<223> OTHER INFORMATION: Amino acid 67-76 deletion of hAChR alpha
      subunit

<400> SEQUENCE: 58
ttacaaccta aaaaaaattc acattcttac aacctaaaaa aaattcacat tcttacaacc     60
taaaaaaaat tcacattc                                                   78

<210> SEQ ID NO 59
<211> LENGTH: 56
<212> TYPE: DNA
<213> ORGANISM: Artificial Sequence
<220> FEATURE:
<223> OTHER INFORMATION: hAChR alpha subunit

<400> SEQUENCE: 59
ttacaaccta aaatggaatc cagatgacta tggcggtgtg aaaaaaattc acattc         56
```

```
<210> SEQ ID NO 60
<211> LENGTH: 52
<212> TYPE: DNA
<213> ORGANISM: Artificial Sequence
<220> FEATURE:
<223> OTHER INFORMATION: amino acid 129-145 deletion of hAChR alpha
      subunit

<400> SEQUENCE: 60
ctactgtctg ggcctactgt ctgggcctac tgtctgggcc tactgtctgg gc            52

<210> SEQ ID NO 61
<211> LENGTH: 64
<212> TYPE: DNA
<213> ORGANISM: Artificial Sequence
<220> FEATURE:
<223> OTHER INFORMATION: hAChR alpha subunit

<400> SEQUENCE: 61
ctactgtgag atcatcgtca cccactttcc ctttgatgaa cagaactgca gcatgaagct    60
gggc                                                                 64
```